US009839349B2

United States Patent
Dejima et al.

(10) Patent No.: US 9,839,349 B2
(45) Date of Patent: Dec. 12, 2017

(54) METHOD OF PLACING MEDICAL INSERTION INSTRUMENTS IN BODY CAVITY

(71) Applicants: FUJIFILM Corporation, Tokyo (JP); THE INSTITUTE FOR CANCER RESEARCH, Philadelphia, PA (US)

(72) Inventors: Takumi Dejima, Ashigarakami-gun (JP); Nobuyuki Torisawa, Ashigarakami-gun (JP); Masayuki Iwasaka, Ashigarakami-gun (JP); Paul Curcillo, Philadelphia, PA (US)

(73) Assignees: FUJIFILM Corporation, Tokyo (JP); THE INSTITUTE FOR CANCER RESEARCH, Philadelphia, PA (US)

( * ) Notice: Subject to any disclaimer, the term of this patent is extended or adjusted under 35 U.S.C. 154(b) by 726 days.

(21) Appl. No.: 14/046,461

(22) Filed: Oct. 4, 2013

(65) Prior Publication Data

US 2014/0100421 A1 Apr. 10, 2014

Related U.S. Application Data

(60) Provisional application No. 61/710,492, filed on Oct. 5, 2012.

(51) Int. Cl.
*A61B 1/313* (2006.01)
*A61B 1/06* (2006.01)
(Continued)

(52) U.S. Cl.
CPC ........ *A61B 1/3132* (2013.01); *A61B 1/00009* (2013.01); *A61B 1/0014* (2013.01);
(Continued)

(58) Field of Classification Search
CPC ............... A61B 17/34; A61B 17/0218; A61B 17/320016–17/32056; A61B 17/00234;
(Continued)

(56) References Cited

U.S. PATENT DOCUMENTS 3,593,706 A * 7/1971 Schubert ............ A61B 1/00165
385/117
4,254,762 A * 3/1981 Yoon .................. A61B 1/00135
600/114

(Continued)

FOREIGN PATENT DOCUMENTS

JP 10-137184 A 5/1998

*Primary Examiner* — Timothy J Neal
*Assistant Examiner* — Aaron B Fairchild
(74) *Attorney, Agent, or Firm* — Birch, Stewart, Kolasch & Birch, LLP

(57) ABSTRACT

An endoscope and an illuminator are safely placed in a body cavity without generating a noticeable postoperative scar. A method of placing medical insertion instruments into a body cavity includes a first step of inserting, into the body cavity through a first opening formed on a body wall, an endoscope together with a first illuminator; and a second step of inserting, into the body cavity through a second opening formed at a position different from the first opening, a second illuminator. Preferably, the method further includes a third step of pulling out the first illuminator from the first opening and inserting the first illuminator into the body cavity through a third opening formed at a position different from the first and second openings.

14 Claims, 22 Drawing Sheets

(51) Int. Cl.
　　　A61B 1/00　　　(2006.01)
　　　A61B 17/00　　(2006.01)
　　　A61B 17/02　　(2006.01)
　　　A61B 90/30　　(2016.01)
　　　A61B 1/05　　　(2006.01)
　　　A61B 1/07　　　(2006.01)
　　　A61B 1/005　　(2006.01)
　　　A61B 17/34　　(2006.01)

(52) U.S. Cl.
　　　CPC ........ *A61B 1/00052* (2013.01); *A61B 1/0057* (2013.01); *A61B 1/00105* (2013.01); *A61B 1/00117* (2013.01); *A61B 1/00158* (2013.01); *A61B 1/05* (2013.01); *A61B 1/06* (2013.01); *A61B 1/0669* (2013.01); *A61B 1/07* (2013.01); *A61B 1/313* (2013.01); *A61B 17/00234* (2013.01); *A61B 17/0218* (2013.01); *A61B 17/3423* (2013.01); *A61B 90/30* (2016.02); *A61B 2017/3445* (2013.01); *A61B 2017/3447* (2013.01)

(58) Field of Classification Search
　　　CPC ...... A61B 17/0225; A61B 2017/00057; A61B 1/0661; A61B 1/00; A61B 1/00105; A61B 1/06; A61B 1/0623; A61B 1/313; A61B 1/3132; A61B 17/3421; A61B 2017/3445; A61B 2017/3447; A61B 2017/3449; A61B 90/30; A61B 90/304; A61B 90/306; A61B 90/308; A61B 90/309; A61B 90/35; A61B 90/36

USPC ....... 600/178, 104, 109, 114, 121, 160, 182, 600/478; 604/164.01, 264; 606/1, 2, 5, 606/16, 27, 127, 129, 171, 180, 191, 198, 606/46, 108, 130; 607/88, 89
See application file for complete search history.

(56) References Cited

U.S. PATENT DOCUMENTS

| | | | | |
|---|---|---|---|---|
| 5,167,220 A | * | 12/1992 | Brown | A61B 1/12 600/156 |
| 5,178,130 A | * | 1/1993 | Kaiya | A61B 1/0005 348/68 |
| 5,879,306 A | * | 3/1999 | Fontenot | A61B 1/3132 600/473 |
| 6,036,637 A | * | 3/2000 | Kudo | A61B 1/00039 600/102 |
| 6,387,044 B1 | * | 5/2002 | Tachibana | A61B 1/00135 600/114 |
| 2003/0135091 A1 | * | 7/2003 | Nakazawa | A61B 1/00073 600/113 |
| 2005/0222534 A1 | * | 10/2005 | Uesugi | A61B 50/13 604/26 |
| 2005/0272975 A1 | * | 12/2005 | McWeeney | A61B 1/00071 600/113 |
| 2007/0100211 A1 | * | 5/2007 | Selover | A61B 17/3421 600/199 |
| 2010/0198014 A1 | * | 8/2010 | Poll | A61B 1/00091 600/123 |
| 2011/0098528 A1 | * | 4/2011 | Lewinsky | A61B 1/0125 600/104 |

* cited by examiner

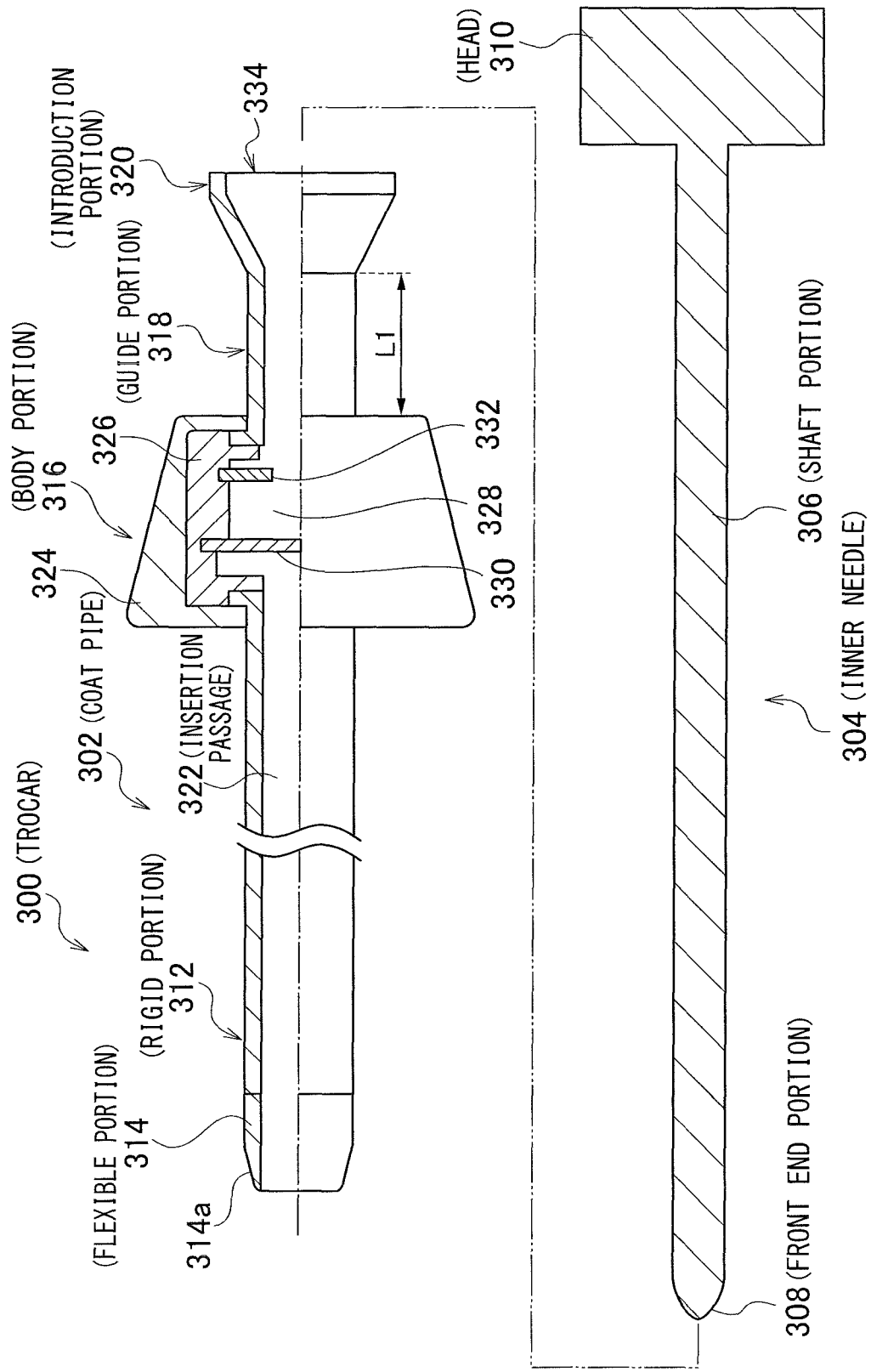

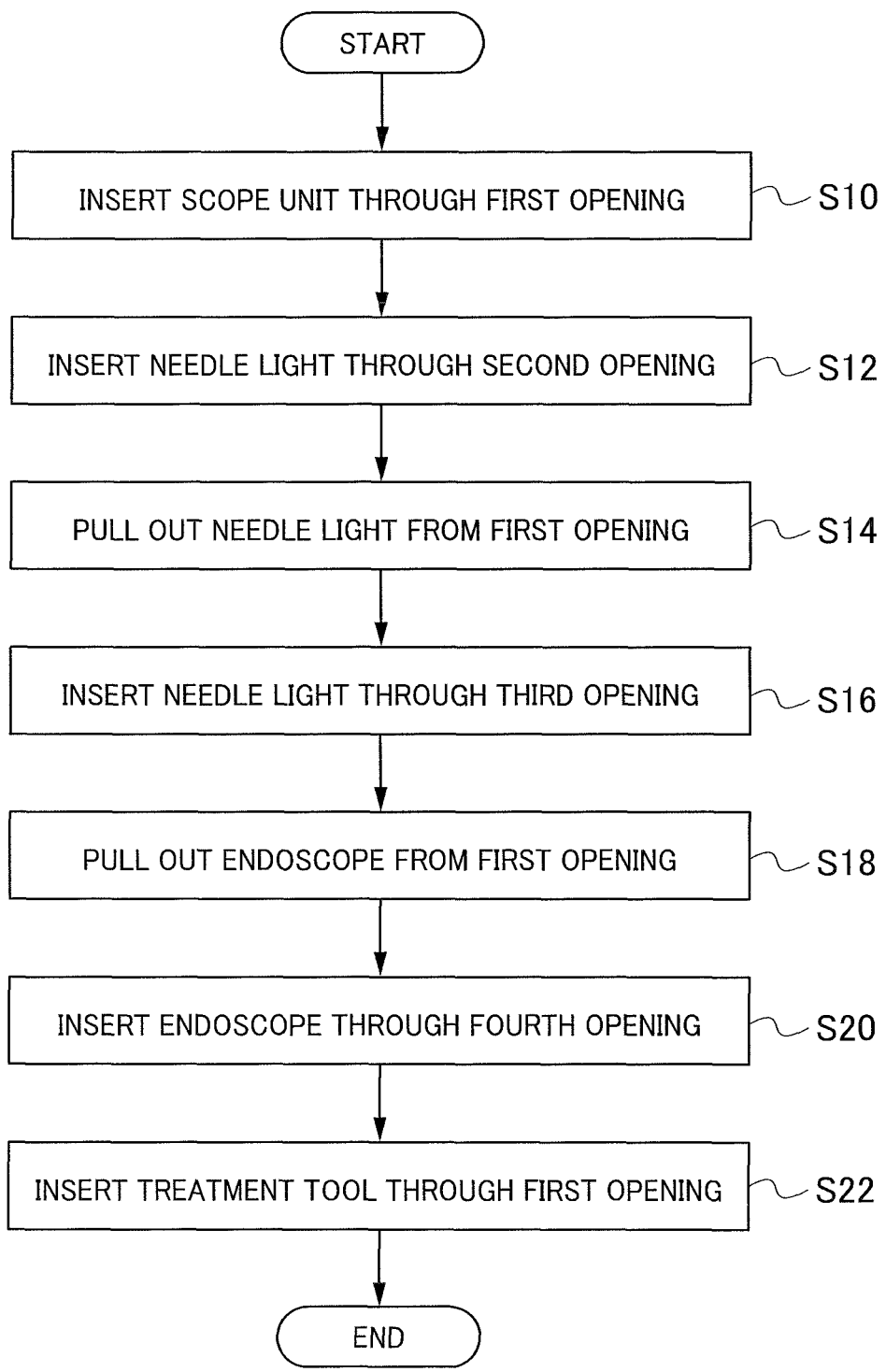

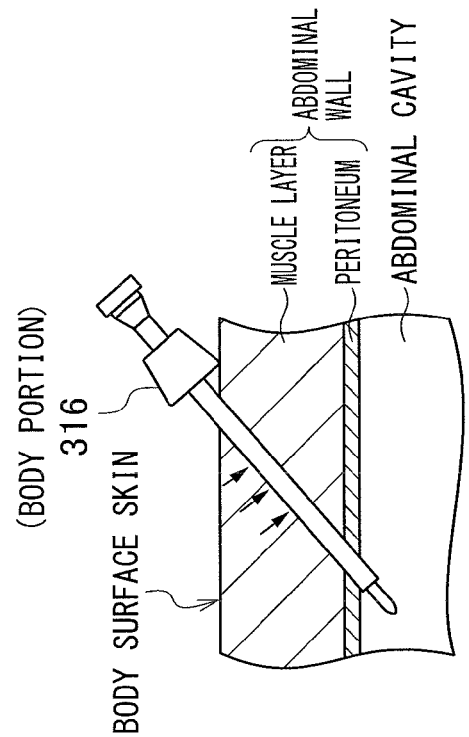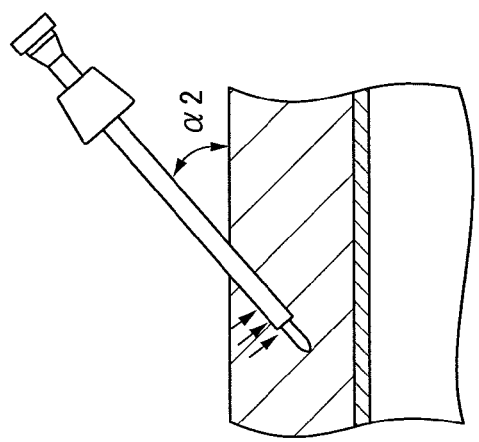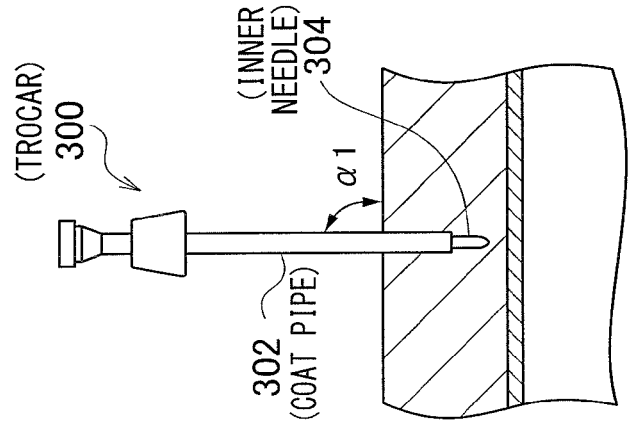

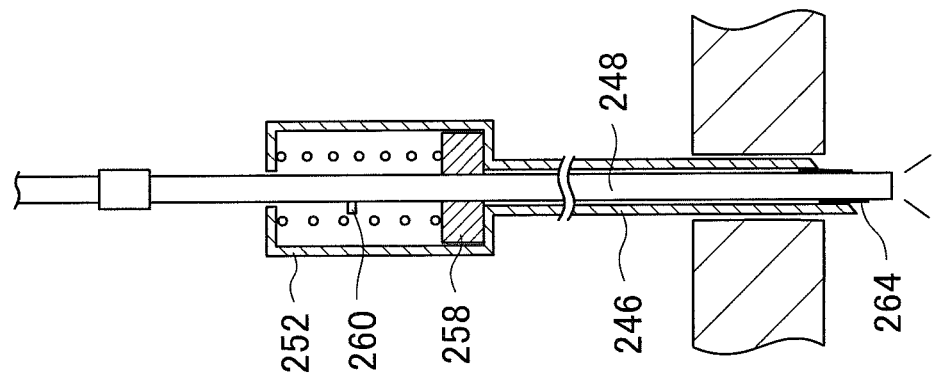
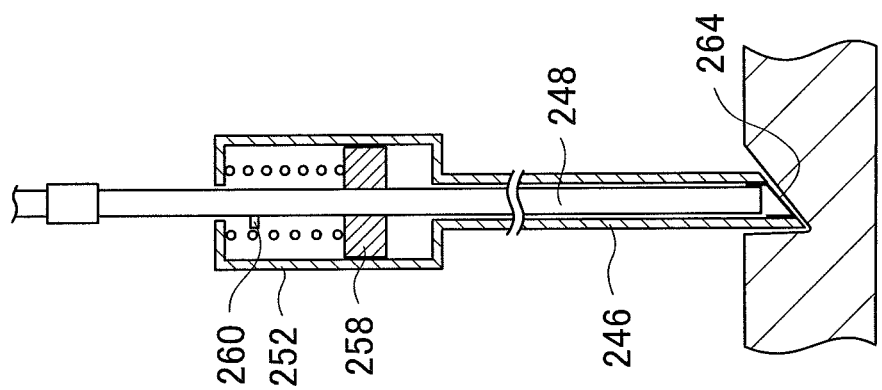
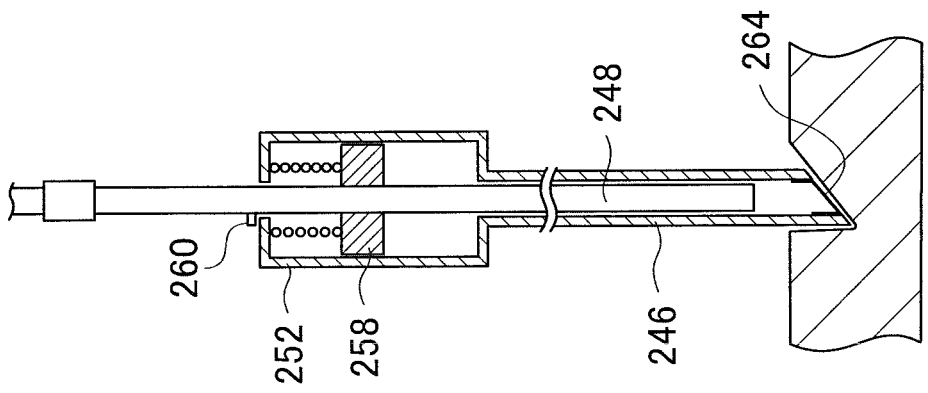

METHOD OF PLACING MEDICAL INSERTION INSTRUMENTS IN BODY CAVITY

CROSS REFERENCE TO RELATED APPLICATIONS

This application claims priority under U.S.C. §119(e) of U.S. Provisional Applications 61/710,492 filed on Oct. 5, 2012 which is incorporated herein by reference in its entirety.

BACKGROUND OF THE INVENTION

Field of the Invention

The present invention relates to a method of placing medical insertion instruments inside a body cavity, and more particularly relates to a method of safely placing into a body cavity an endoscope for observing the inside of the body cavity and an illuminator configured separately from the endoscope to emit illumination light for illuminating the inside of the body cavity.

Description of the Related Art

In recent years, endoscopic surgery using a rigid endoscope (rigid mirror) such as an abdominoscope is widely performed since the endoscopic surgery is less invasive to a patient than surgery involving operation such as laparotomy and thoracotomy. For example, in laparoscopic surgery, a cylindrical trocar is pierced into several places on an abdominal region of a patient, and an endoscope (abdominoscope), treatment tools and the like are inserted into an abdominal cavity through the trocar, so that treatment is performed with use of the treatment tools while an endoscope image is observed with a monitor.

Recently, single port surgery (SPS) that is laparoscopic surgery performed with one hole formed on an umbilical region is also rapidly spreading. Since only one postoperative scar is left in an umbilical region in the single port surgery, it is less distinctive, and therefore the surgery is excellent in terms of cosmetics.

However, in the single port surgery, only one opening (insertion hole) is formed on a body wall for access into a body cavity, the endoscope and the treatment tools tend to interfere inside and outside the body cavity, which tends to constrain operation of these tools. When the endoscope and the treatment tools interfere, it may become impossible to position the endoscope at a location convenient for observation, which may hinder observation and treatment of a treatment target region.

Under these circumstances, a demand for reduction in diameter of an insertion portion of the endoscope is increasing. If the diameter of the insertion portion of the endoscope can be reduced, an opening for the endoscope can be downsized even when it is formed in portions other than the umbilical region, so that a postoperative scar can be made less noticeable. Moreover, it becomes possible to solve failures in the aspect of operation and observation as compared with the case of accessing into a body cavity through one opening.

Generally, the endoscope has a function of observing an inside of a body cavity as well as a function of illuminating the inside of the body cavity. More specifically, a light guide for transmitting illumination light from a light source device is inserted to and placed at an insertion portion of the endoscope, and the illumination light emitted from an emitting end of the light guide is made to irradiate the inside of the body cavity through an illumination window. Accordingly, if the insertion portion of the endoscope is made too small, enough occupation space for inserting and placing the light guide is not secured, which causes insufficient brightness of the illumination light.

On the contrary, Japanese Patent Application Laid-Open No. 10-137184 discloses a system including an endoscope to observe an inside of a body cavity and an illuminator (illumination probe) configured separately from the endoscope to illuminate the inside of the body cavity. In this system, illumination light from one light source device is dividedly fed to the endoscope and to the illuminator through a light guide cable, so that the illumination light emitted from the endoscope and the illuminator can illuminate the inside of the body cavity.

SUMMARY OF THE INVENTION

According to the system disclosed in the Japanese Patent Application Laid-Open No. 10-137184, even when the illumination light emitted from the endoscope has insufficient brightness, desired brightness can be obtained by the illumination light emitted from the illuminator. Moreover, since an observation position can be irradiated with the illumination light from various directions, it becomes much easier to observe the observation position.

However, if the insertion portion of the endoscope is made too small in the system disclosed in Japanese Patent Application Laid-Open No. 10-137184, a problem of insufficient brightness of the illumination light arises as mentioned above. Accordingly, when it is attempted to insert the endoscope into a body cavity before the illuminator is guided into the body cavity, it becomes difficult to observe the state of the body cavity with a monitor due to the insufficient brightness of the illumination light. Therefore, it is difficult to safely place the endoscope in a desired position inside the body cavity.

It can also be considered to place the illuminator in the body cavity before the endoscope, though the illuminator does not include a function of observing the inside of the body cavity, and therefore it is impossible to insert the illuminator into the body cavity while observing the state inside the body cavity with the monitor. Accordingly, a front end of the illuminator may come into contact with an organ, and may cause organ damage thereby.

The present invention has been made in view of such circumstances and an object of the present invention is to provide a method of safely placing an endoscope and an illuminator in a body cavity without generating a noticeable postoperative scar.

In order to achieve the above object, the present invention includes: a first step of inserting, into a body cavity through a first opening formed on a body wall, an endoscope configured to observe an inside of the body cavity together with a first illuminator configured separately from the endoscope to emit illumination light to illuminate the inside of the body cavity; and a second step of inserting, into the body cavity through a second opening formed at a position different from the first opening, a second illuminator configured separately from the endoscope to emit illumination light to illuminate the inside of the body cavity.

A preferable aspect of the present invention further includes a third step of pulling out the first illuminator from the first opening and inserting the first illuminator into the body cavity through a third opening formed at a position different from the first and second openings. Moreover, it is preferable that the aspect further includes a fourth step of pulling out the endoscope from the first opening and inserting the endoscope into the body cavity through a fourth opening formed at a position different from the first to third openings, and it is more preferable that the aspect further includes a sixth step of inserting a treatment tool into the body cavity through the first opening after the endoscope is pulled out.

In a preferable aspect of the present invention, the second to fourth openings are smaller than the first opening.

In a preferable aspect of the present invention, the endoscope does not include illumination means configured to illuminate the inside of the body cavity.

In a preferable aspect of the present invention, an insertion portion of the endoscope that is inserted into the body cavity has an external diameter of 3 mm or less.

In a preferable aspect of the present invention, insertion portions of the first and second illuminators that are inserted into the body cavity have an external diameter of 3 mm or less.

According to the present invention, even when illumination light of the endoscope has insufficient brightness, it becomes possible to safely place the endoscope and the illuminator in desired positions while constantly observing and illuminating the inside of the body cavity with the endoscope and the illuminator. Moreover, even when an increased number of openings are formed on a body wall, the second to fourth openings are openings for guiding the endoscope and the illuminator into the body cavity, so that these openings can be downsized. This makes it possible to make a postoperative scar less noticeable and to reduce the burden of a patient.

BRIEF DESCRIPTION OF THE DRAWINGS

FIG. 4 is a schematic view illustrating a configuration example of a trocar;

FIG. 5 is a flowchart illustrating procedures for inserting body-cavity insertion instruments into an abdominal cavity;

FIGS. 12A to 12C are explanatory views for explaining a method of inserting a trocar;

FIGS. 23A to 23C are explanatory views illustrating the needle light according to the fifth embodiment being inserted into an abdominal wall.

DETAILED DESCRIPTION OF THE PREFERRED EMBODIMENTS

Hereinafter, preferable embodiments of the present invention are described in detail with reference to accompanying drawings.

First Embodiment

[Medical Observation System]

Figure 1:
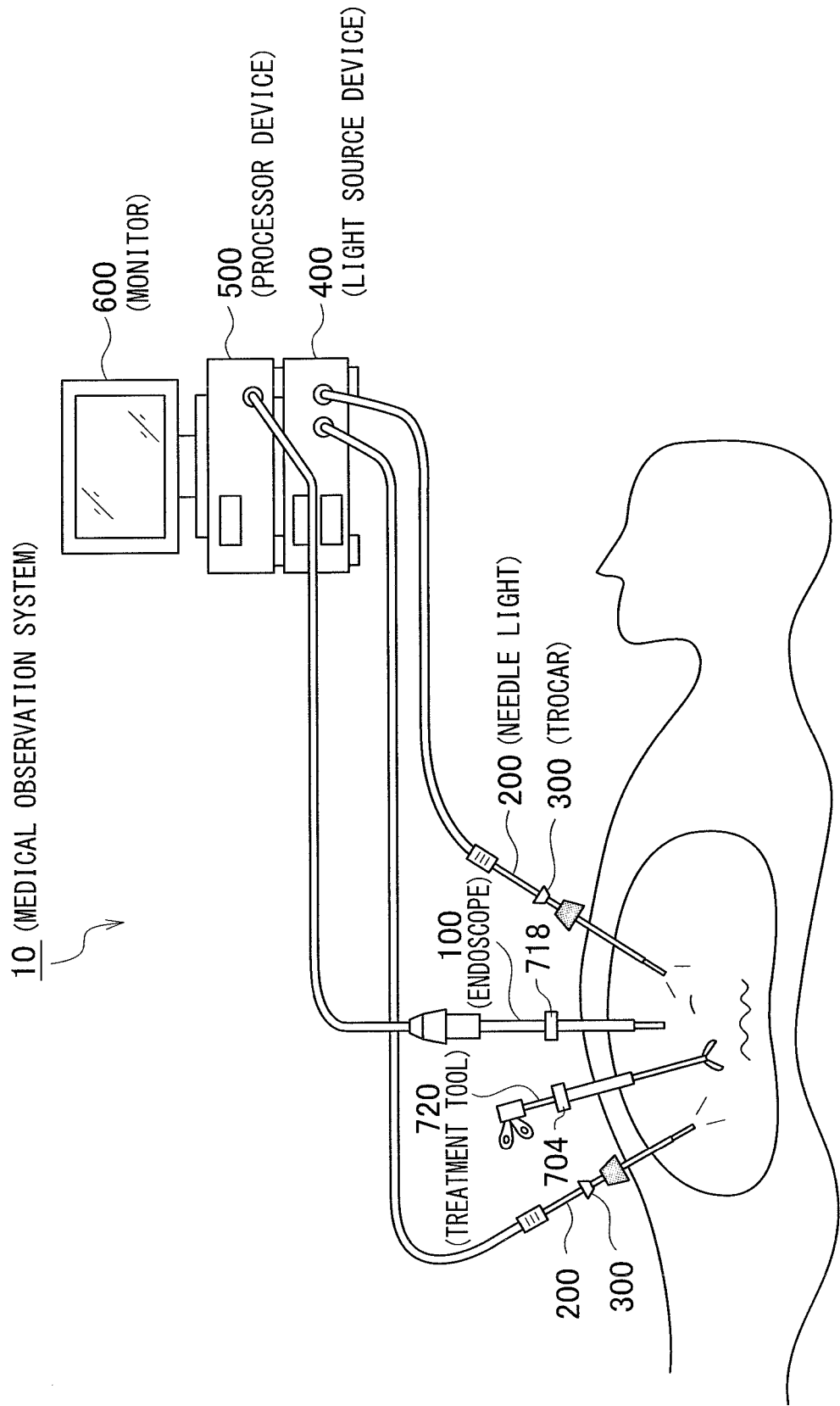
FIG. 1 is an overall configuration view illustrating one embodiment of a medical observation system.

FIG. 1 is an overall configuration view illustrating one embodiment of a medical observation system. As illustrated in FIG. 1, the medical observation system 10 of the present embodiment includes an endoscope 100 configured to observe an observation target portion in a body cavity, a needle light (illuminator) 200 configured to irradiate the body cavity of a subject with illumination light, a light source device 400 configured to supply illumination light to the needle light 200, and a processor device 500 configured to generate an endoscope image. The processor device 500 is connected to a monitor 600 configured to display the endoscope image.

[Endoscope]

Figure 2:
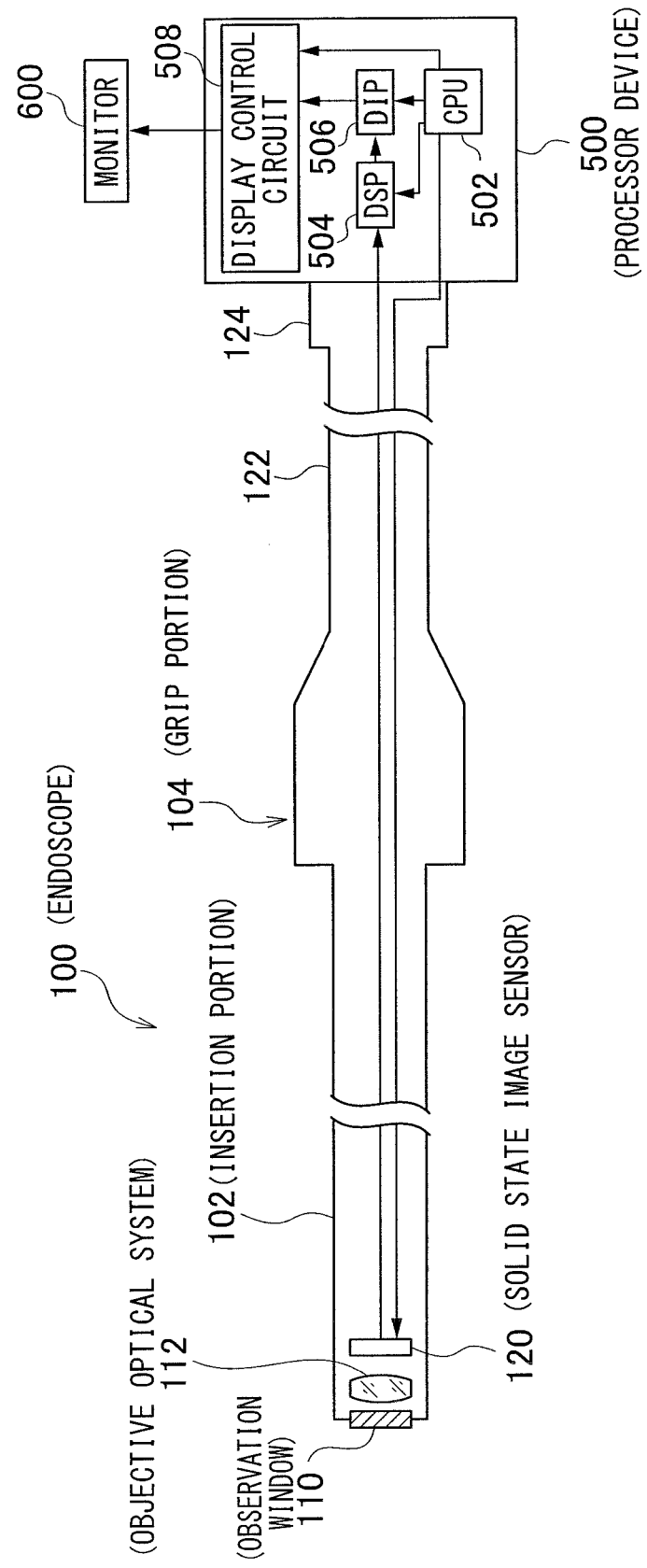
FIG. 2 is a schematic view illustrating a configuration example of an endoscope.

FIG. 2 is a schematic view illustrating a configuration example of the endoscope 100. The endoscope (electronic endoscope) 100 illustrated in FIG. 2 includes a rigid insertion portion 102 that is inserted into a body cavity of the subject, a grip portion 104 provided in a back end of the insertion portion 102, and a signal cable 122 extendedly provided from the back end of the grip portion 104. At the end of the signal cable 122, a connector 124 removably connected to the processor device 500 is provided.

An observation window 110 configured to take in image light of an object is mounted on the front end of the insertion portion 102. Behind the observation window 110, an objective optical system 112 and a solid state image sensor 120 (such as a CMOS sensor and a CCD sensor) are placed. Object light passing through the observation window 110 and the objective optical system 112 is incident into an imaging surface (light receiving surface) of the solid state image sensor 120. The solid state image sensor 120 performs photoelectric conversion of the incident object light, and outputs a converted electrical signal (imaging signal). The electrical signal outputted from the solid state image sensor 120 is inputted into the processor device 500 through the signal cable 122 and the connector 124.

As illustrated in FIG. 2, the processor device 500 includes a CPU 502, a DSP 504, a DIP 506 and a display control circuit 508. The CPU 502 integrally controls operation of the entire processor device 500.

The DSP 504 performs various signal processings, such as color separation, color interpolation, gain correction, white balance adjustment, and gamma control, on the electrical signal outputted from the solid state image sensor 120 to generate image data. The image data generated in the DSP 504 is inputted into the DIP (digital image processing circuit) 506.

The DIP 506 performs electronic variable magnification, or various image processings such as color enhancement and edge enhancement, on the image data processed in the DSP 504. The image data subjected to various image processings in the DIP 506 is inputted into the display control circuit 508.

The display control circuit 508 converts the image data from the DIP 506 into a video signal corresponding to a signal format supported by the monitor 600, and outputs it to the monitor 600. As a consequence, an observation image (endoscope image) is displayed on the monitor 600.

In the present embodiment, the insertion portion 102 of the endoscope 100 does not include an illumination means configured to illuminate an inside of a body cavity. That is, it does not have an illumination window and a light guide which are included in common endoscopes, and an occupation space for placing these members is unnecessary. Accordingly, an external diameter of the insertion portion 102 can be reduced, so that an opening (insertion hole) formed on a body wall for guiding the insertion portion 102 into a body cavity can be downsized. This makes it possible to make a postoperative scar less noticeable and to thereby reduce the burden on the subject.

In the present embodiment, an external diameter of the insertion portion 102 is preferably 3 mm or less. In this example, the external diameter of the insertion portion 102 is set to 2.9 mm. By setting the external diameter of the insertion portion 102 to 3 mm or less, an opening (insertion hole) formed on a body wall for guiding the insertion portion 102 into the body cavity can be downsized. As a result, it becomes unnecessary to suture the opening, and therefore a postoperative scar can be made less noticeable. If the external diameter of the insertion portion 102 is made too small, a sufficient occupation space for built-in objects (such as an image guide) that are built in the inside of the insertion portion 102 cannot be secured, and therefore it is preferable that the external diameter of the insertion portion 102 is 2 mm or more.

[Needle Light]

Figure 3:
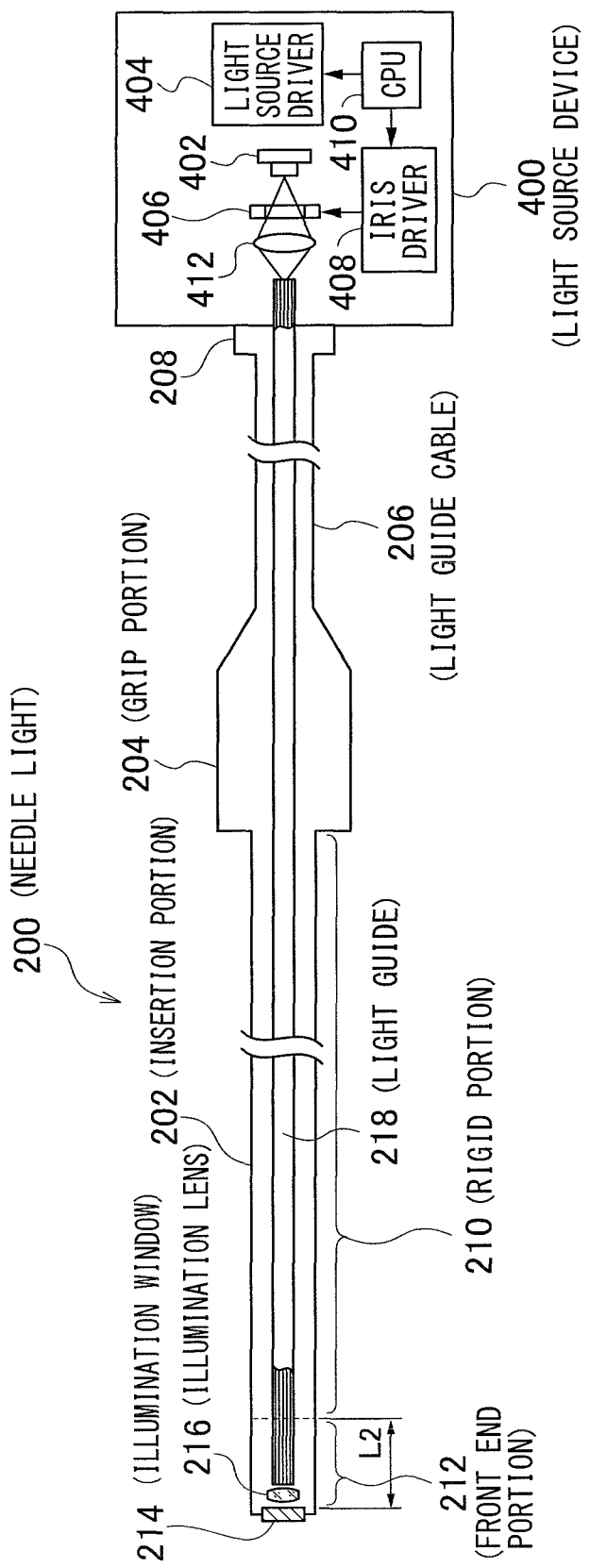
FIG. 3 is a schematic view illustrating a configuration example of a needle light.

FIG. 3 is a schematic view illustrating a configuration example of the needle light 200. As illustrated in FIG. 3, the needle light 200 includes an insertion portion 202 that is inserted into a body cavity, a grip portion 204 provided in a back end of the insertion portion 202, and a light guide cable 206 extendedly provided from the back end of the grip portion 204. At the end of the light guide cable 206, a light source connector 208 removably connected to the light source device 400 is provided.

The insertion portion 202 includes an oblong and lengthy rigid portion 210 and a front end portion 212 which is provided at the front end of the rigid portion 210 and which is more flexible than the rigid portion 210. As one method of forming the insertion portion 202, there is a method in which a flexible pipe is bonded to the front end of a rigid pipe with adhesives or with solder. A reinforcement pipe made of metal and the like may be provided onto the flexible pipe (soft pipe) except a front end portion of the flexible pipe. The front end portion of the rigid pipe (hard pipe) may be thinned or be provided with a slit.

An illumination window 214 is mounted on a front end surface of the insertion portion 202 (front end portion 212). Behind the illumination window 214, an illumination lens 216 is placed configured to emit illumination light toward the inside of the body cavity. The illumination lens 216 faces an emitting end of a light guide 218. The light guide 218 is inserted into the insertion portion 202, the grip portion 204, and the light guide cable 206, so that an incident end thereof is exposed from the end of the light source connector 208. When the light source connector 208 is connected to the light source device 400, the incident end of the light guide 218 is inserted into the light source device 400. The illumination light from the light source device 400 is guided by the light guide 218 to the front end portion 212 so as to irradiate the inside of the body cavity through the illumination lens 216 and the illumination window 214.

As illustrated in FIG. 3, the light source device 400 includes a light source 402, a light source driver 404, an aperture adjustment mechanism 406, an iris driver 408, and a CPU 410 which controls these component members. The light source 402 is turned on and off under control of the light source driver 404 and emits illumination light toward a condenser lens 412 positioned ahead. As the light source 402, a xenon lamp, a halogen lamp, an LED (light emitting diode), a fluorescent light emitting element, or an LD (laser diode) can be used for example. The light source 402 is properly selected depending on the type of an endoscope image (visible image, fluorescence images and the like) to be picked up, i.e., depending on a wavelength to be used.

The aperture adjustment mechanism 406 is placed between the light source 402 and the condenser lens 412 to adjust a light volume of the illumination light so that an endoscope image picked up by the solid state image sensor 120 (see FIG. 2) of the endoscope 100 has generally constant brightness. The aperture adjustment mechanism 406 includes an aperture blade configured to change a diameter of an aperture opening (aperture diameter) for passing the illumination light, and a motor configured to drive the aperture blade. The iris driver 408 opens and closes the aperture blade of the aperture adjustment mechanism 406 to change a passage area of the illumination light so as to adjust the light volume of the illumination light incident into the light guide 218.

In the present embodiment, an external diameter of the insertion portion 202 is preferably 3 mm or less, and more preferably 2.3 mm or less. In this example, the external diameter of the insertion portion 202 is 2.1 mm. Consequently, as in the case of the insertion portion 102 of the endoscope 100, an opening (insertion hole) formed on a body wall for guiding the insertion portion 202 into a body cavity can be downsized, and thereby a postoperative scar can be made less noticeable.

It is to be noted that in the present embodiment, the rigid portion 210 is provided in the insertion portion 202, though it is not limited thereto, it may have an elastic portion having flexibility in place of the rigid portion 210.

Moreover, in the present embodiment, although the needle light 200 is illustrated to be configured such that the illumination light from the light source device 400 is guided to the front end portion 212 by the light guide 218 and is emitted to the inside of the body cavity through the illumination lens 216 and the illumination window 214, it is not limited thereto, the configuration of the needle light may be such that an LED light source is built in the top end of the needle light.

[Trocar]

FIG. 4 is a schematic view illustrating a configuration example of a trocar 300. As illustrated in FIG. 4, the trocar 300 which is a guide member configured to guide the needle light 200 into a body cavity, includes a coat pipe 302 and an inner needle 304.

The inner needle 304, which is to be inserted into the coat pipe 302, includes a shaft portion 306 formed to be oblong, a front end portion 308 formed at the front end of the shaft portion 306, and a head 310 provided on the base end side of the shaft portion 306. In this example, the shaft portion 306 of the inner needle 304 has an external diameter of 2.1 mm.

The front end portion 308 is dulled into a curved surface shape having no edge (i.e., formed into a roundish non-edge shape) while being capable of easily penetrating a body wall. The shaft portion 306 has an external diameter slightly smaller than an inner diameter of the coat pipe 302. The head 310 is formed into a cylindrical shape which is thicker than the shaft portion 306. When the inner needle 304 is inserted into the coat pipe 302, the head 310 is brought into contact with an end face of the base end side of the coat pipe 302 with the front end portion 308 of the inner needle 304 projecting by a prescribed length from the front end of the coat pipe 302.

The coat pipe 302 includes an oblong rigid portion 312 formed from hard resin, metal and the like, an flexible portion 314 coupled to the front end side of the rigid portion 312, a body portion 316 coupled to the base end side of the rigid portion 312, a guide portion 318 coupled to the base end side of the body portion 316, and an introduction portion 320 provided on the base end side of the guide portion 318. The rigid portion 312, the flexible portion 314, the body portion 316, the guide portion 318, and the introduction portion 320 are coaxially placed, with an insertion passage 322 formed inside these portions so that the needle light 200 and the inner needle 304 can be inserted therein. In this example, the rigid portion 312 has an external diameter of 2.3 mm.

The flexible portion 314 is formed of a flexible member such as rubber and flexible resin. The flexible portion 314 may be made of the same material as the rigid portion 312 (i.e., hard resin, metal and the like), and may be configured to have a plurality of slits (thin grooves) formed on its outer periphery in a circumferential direction or a shaft direction, or in other directions so that the flexible portion 314 is more flexible than the rigid portion 312. A front end portion 314a of the flexible portion 314 is formed in a tapered shape with a thickness continuously decreased over a prescribed length, so that flexibility (plasticity) is higher on the front end side. In addition, corners of the front end portion 314a are formed into a roundish non-edge shape. Therefore, when the flexible portion 314 placed at the front end part of the coat pipe 302 comes into contact with an organ in the state where the inner needle 304 has been pulled out from the coat pipe 302 stuck into a body cavity, damage of the organ can be prevented since the flexible portion 314 deforms itself because of its flexibility.

A reinforcement pipe made of metal and the like may be provided onto the flexible pipe (soft pipe) except a front end portion of the flexible pipe. The front end portion of the rigid pipe (hard pipe) may be thinned or be provided with a slit.

The rigid portion 312 is a portion formed in a region which is to be enclosed with a body wall when the coat pipe 302 is stuck into a body cavity, and the rigid portion 312 is formed of a hard member such as hard resin and metal. Therefore, when the trocar 300 is fed to a prescribed position inside a body cavity and then the inner needle 304 is pulled out from the coat pipe 302, the coat pipe 302 receives pressure force from the body wall, but the rigid portion 312 prevents the coat pipe 302 from being deformed by the pressure force, and therefore it becomes possible to smoothly insert the needle light 200 into the coat pipe 302.

The body portion 316 includes an elastic body layer 324 provided on the entire surface of the body portion 316 and an inner pipe portion 326 provided inside the elastic body layer 324.

The elastic body layer 324 is, for example, made of an elastic member such as rubber and sponge. Since the elastic body layer 324 functions as a means to absorb pressure exerted on a patient, it is preferably formed with a relatively large thickness. As a consequence, when the coat pipe 302 is stuck into a body cavity and the body portion 316 of the coat pipe 302 is in contact with a body wall for a long time and thereby applies pressure thereto, the elastic body layer 324 absorbs and alleviates the pressure, and this makes it possible to reduce the burden to the patient and to achieve low invasiveness.

The inner pipe portion 326 is formed of a hard member such as hard resin and metal as in the case of the rigid portion 312. The inner pipe portion 326 may be configured integrally with the rigid portion 312, and may be configured separately. In the latter case, the inner pipe portion 326 and the rigid portion 312 are coupled with adhesives, solder and the like.

Formed in the inner pipe portion 326 is an inner pipe way 328 which constitutes a part of the insertion passage 322. The inner pipe way 328 has a check valve 330 and a sealing member 332 provided side by side in a shaft direction. The check valve 330 is for preventing compressed air in the body cavity from leaking out of the body in the state where the needle light 200 or the inner needle 304 has been pulled out of the coat pipe 302. The sealing member 332 is placed much closer to the base end side than the check valve 330 and seals a clearance between the needle light 200 or the inner needle 304 and the inner pipe way 328 when the needle light 200 or the inner needle 304 is inserted into the coat pipe 302. The check valve 330 and the sealing member 332 are, for example, made of an elastic member such as rubber.

The guide portion 318 is configured to have an inner diameter slightly larger than an external diameter of the insertion portion 202 of the needle light 200 and to have a prescribed length (guide length L1) in the shaft direction. It is preferable that the guide length L1 of the guide portion 318 is configured to be at least equal to or more than a length L2 along a shaft direction (see FIG. 3) of the front end portion 212 of the insertion portion 202 in the needle light 200. Accordingly, when the front end portion 212 of the insertion portion 202 receives large resistance as it passes the check valve 330 and the sealing member 332 at the time of inserting the insertion portion 202 into the coat pipe 302, the insertion portion 202 can easily be pushed toward the front end side without causing buckle-deformation of the front end portion 212.

The guide portion 318 is formed of a hard member such as hard resin and metal, as in the case of the rigid portion 312 and the inner pipe portion 326. The guide portion 318 may be configured integrally with the inner pipe portion 326, and may be configured separately. In the latter case, the guide portion 318 and the inner pipe portion 326 are coupled with adhesives, solder and the like. It should naturally be understood that the rigid portion 312, the inner pipe portion 326, and the guide portion 318 may be configured integrally.

A conical introduction portion 320 having an inner diameter larger than that of the guide portion 318 is integrally provided on the base end side of the guide portion 318. An opening 334 for inserting the needle light 200 and the inner needle 304 into the coat pipe 302 is formed on an end face of the base end side of the introduction portion 320, and the opening 334 is configured to communicate with the insertion passage 322. The introduction portion 320 is formed gradually expanded toward the base end side, so that the needle light 200 and the inner needle 304 can easily be guided to the insertion passage 322 from the opening 334 of the introduction portion 320.

In a method of using the thus-configured trocar 300, first, the inner needle 304 is inserted into the coat pipe 302, and the front end portion 308 of the inner needle 304 is made to project from the front end of the coat pipe 302. Then, the front end of the inner needle 304 incorporated into the coat pipe 302 is directly stuck into a specified depth position through a body surface skin. The inner needle 304 is then pulled out from the coat pipe 302. Then, the insertion portion 202 of the needle light 200 is inserted into the coat pipe 302, so that the insertion portion 202 of the needle light 200 can be guided into the body cavity.

In the present embodiment, publicly known trocars are used as the trocars 718 and 704 (see FIG. 1) which are guide members configured to guide the endoscope 100 and the treatment tool 720 into the body cavity, and so a description of their configuration is omitted. Generally, trocars are made up of a coat pipe and an inner needle as in the above-described trocar 300, and includes a type of trocar which is stuck into a body cavity through a region partially incised with a scalpel and the like, and a type of trocar which is stuck into a body cavity directly from a body surface skin without any incision or with very small incision, and any of these types can be used.

[Method of Placing Body-Cavity Insertion Instruments]

The medical observation system 10 in the present embodiment configured as described above is used for laparoscopic surgery for treatment of an abdominal cavity that is one of the body cavities of a patient. A detailed description is now given of a method of placing in an abdominal cavity that is a body cavity of a patient the body-cavity insertion instruments (endoscope 100 and needle light 200) of the medical observation system 10 in the present embodiment for laparoscopic surgery with reference to FIG. 5 to FIG. 11B.

Figure 6D:
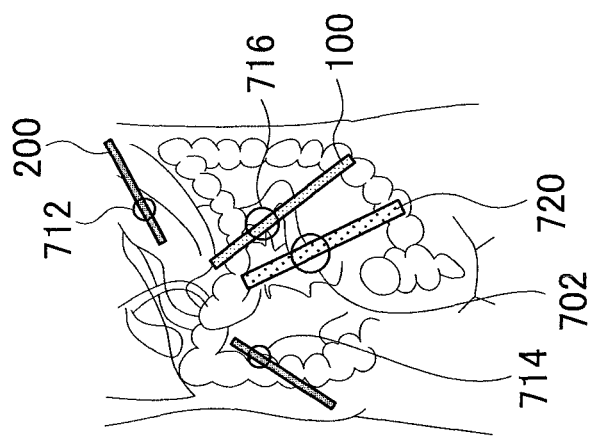
FIGS. 6A to 6D are plan views schematically illustrating the body-cavity insertion instruments being inserted into an abdominal cavity.
Figure 6C:
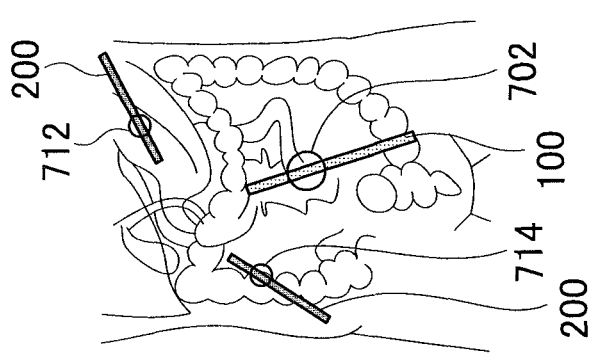
Figure 6B:
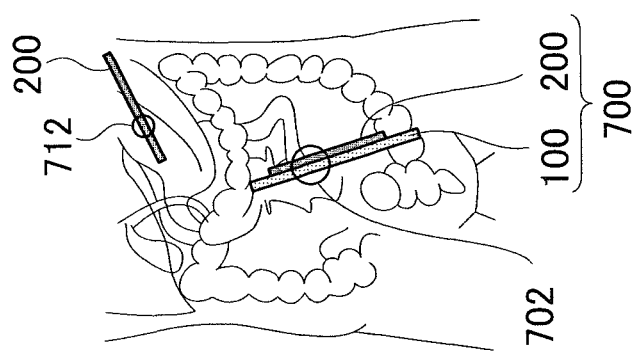

FIG. 5 is a flowchart illustrating procedures for inserting into the abdominal cavity the body-cavity insertion instruments included in the medical observation system 10 of the present embodiment. FIGS. 6A to 6D are plan views schematically illustrating the body-cavity insertion instruments being inserted into the abdominal cavity. FIG. 7 is a cross sectional view schematically illustrating the body insertion instruments being inserted into the abdominal cavity. It is to be noted that a series of steps illustrated in FIG. 5 are steps in consideration of low invasiveness in addition to safety.

Figure 6A:
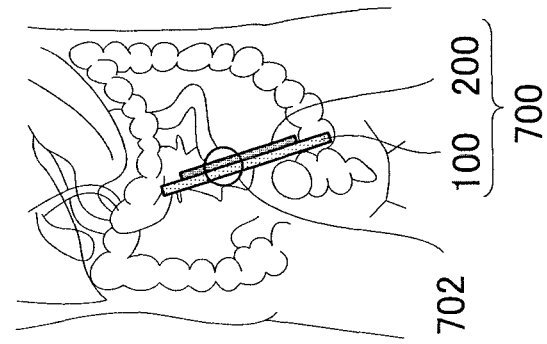
Figure 7:
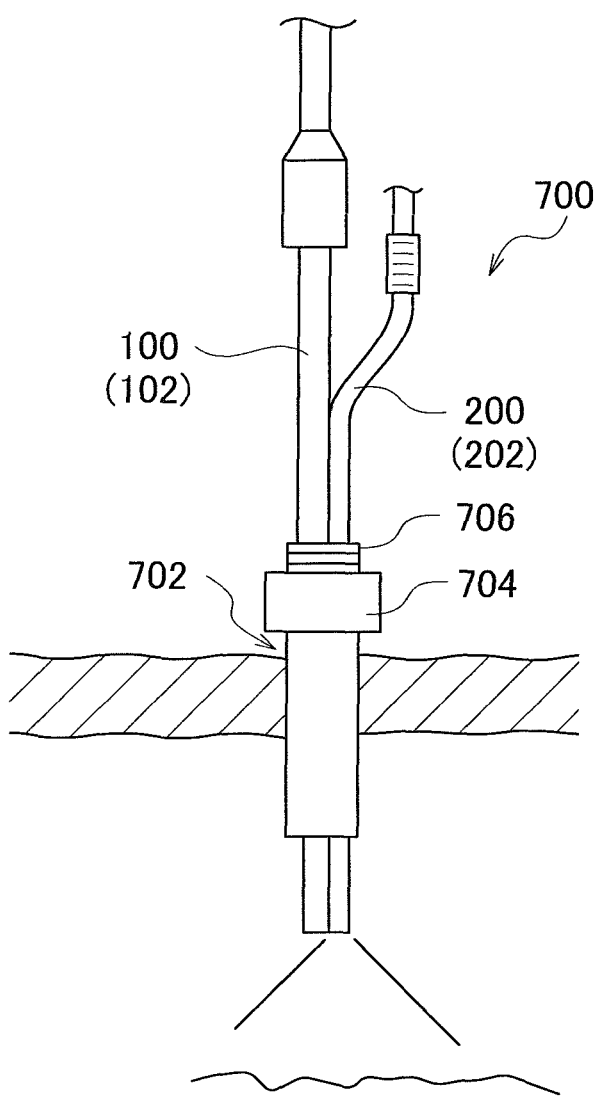
FIG. 7 is a cross sectional view schematically illustrating the body insertion instruments being inserted into an abdominal cavity.

First, as illustrated in FIG. 6A and FIG. 7, a scope unit 700 integrating the insertion portion 102 of the endoscope 100 and the insertion portion 202 of the needle light 200 is inserted into an abdominal cavity through a first opening (insertion hole) 702 formed on an abdominal wall (Step S10 of FIG. 5).

The first opening 702 is an opening formed in an abdomen (for example, umbilical region) of a patient for inserting treatment tools, such as forceps, into the abdominal cavity. A trocar 704 (for example, 5-mm forceps trocar) of a size corresponding to an external diameter of a treatment tool is inserted through the first opening 702, and the scope unit 700 is inserted into the abdominal cavity through the trocar 704.

In general laparoscopic surgery, at least one set of 5-mm forceps is needed. Step S10 of FIG. 5 is a technique step using the 5-mm forceps trocar, and, by inserting a 2.9-mm scope and a 2.1-mm needle light (2.9+2.1=5 mm) together into the 5-mm forceps trocar, less invasive preparation (trocar placement) for treatment can be performed without forming an unnecessary opening (insertion hole) on the abdominal wall.

Figure 8:
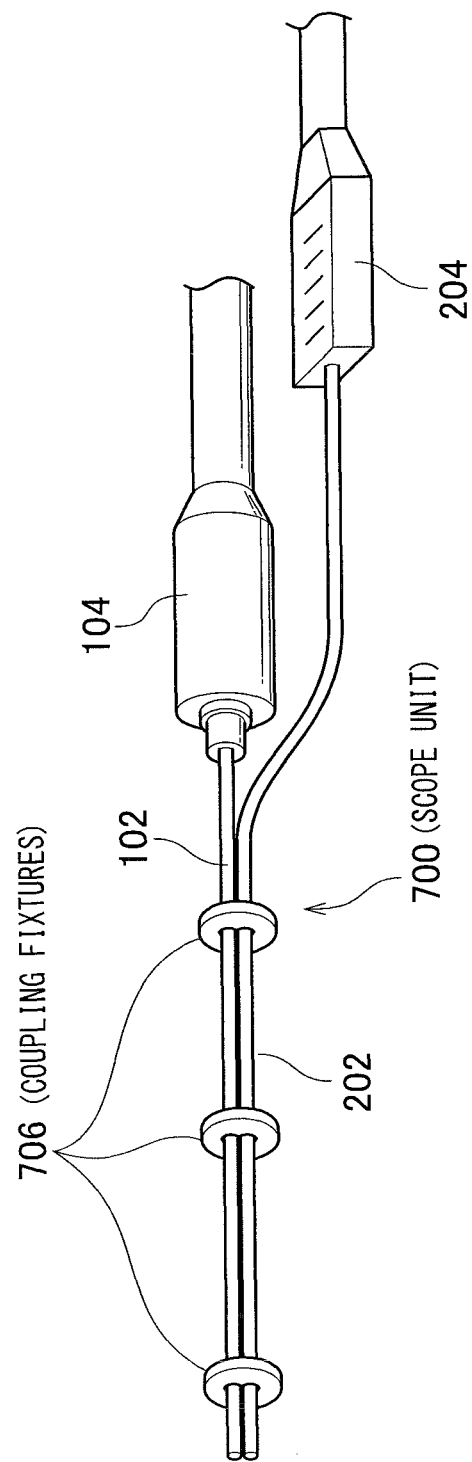
FIG. 8 is a schematic view illustrating a scope unit.
Figure 9:
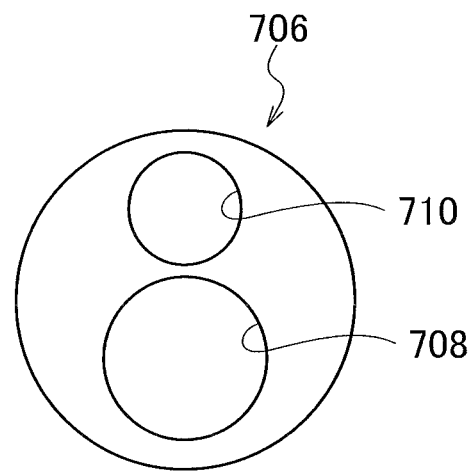
FIG. 9 is a plan view illustrating a configuration example of coupling fixtures.
Figure 10:
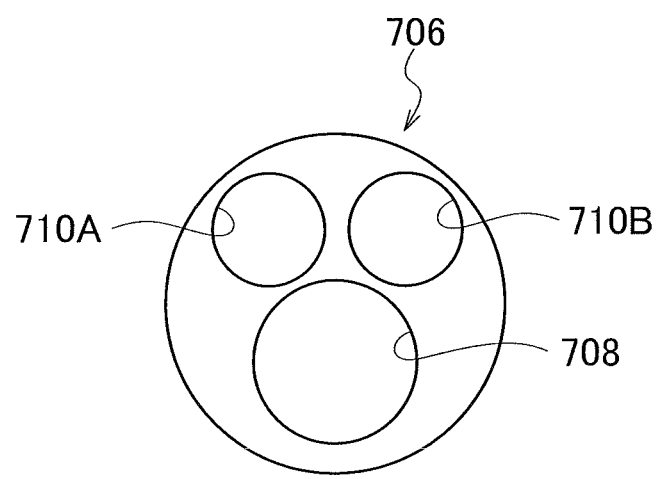
FIG. 10 is a plan view illustrating another configuration example of the coupling fixtures.

FIG. 8 is a schematic view illustrating the scope unit 700. FIG. 9 is a plan view illustrating a configuration example of coupling fixtures 706. As illustrated in FIG. 9 and FIG. 10, the scope unit 700 is composed of the insertion portion 102 of the endoscope 100 and the insertion portion 202 of the needle light 200 integrated with a plurality of coupling fixtures (retaining members) 706 placed at specified intervals along with a longitudinal direction of the insertion portion 102 of the endoscope 100. Each coupling fixture 706 is configured for the respective insertion portions 102 and 202 to be slidable along the longitudinal direction of these portions.

The coupling fixture 706 is constituted of a thin-plate disc-like member made of, for example, a resin material such as plastic. Two through holes 708 and 710 different in inner diameter are formed in the coupling fixture 706. Out of these through holes 708 and 710, the first through hole 708 with a larger inner diameter is a hole portion for inserting the insertion portion 102 of the endoscope 100, and the inner diameter thereof is slightly larger than the external diameter of the insertion portion 102 of the endoscope 100. The second through hole 710 with a smaller inner diameter is a hole portion for inserting the insertion portion 202 of the needle light 200, and the inner diameter of the second through hole 710 is slightly larger than the external diameter of the insertion portion 202 of the needle light 200.

The insertion portions 102 and 202 are inserted through the respective through holes 708 and 710 of a plurality of the thus-configured coupling fixtures 706, and in this state the coupling fixtures 706 are placed side by side at specified intervals along with the longitudinal direction of the insertion portion 102 of the endoscope 100 as illustrated in FIG. 8, and therefore the insertion portion 102 of the endoscope 100 and the insertion portion 202 of the needle light 200 are integrated with their shaft directions parallel to each other and their shafts being close to each other.

If the scope unit 700 integrally formed as described above is inserted into the trocar 704, the respective coupling fixtures 706 come into contact with the end face of the base end side of the trocar 704 and are piled on top of each other without entering into the trocar 704 as illustrated in FIG. 7. The insertion portion 102 of the endoscope 100 and the insertion portion 202 of the needle light 200 are guided into the abdominal cavity while being parallel to each other with the trocar 704. Therefore, by inserting the scope unit 700 integrally configured with a plurality of the coupling fixtures 706 into the trocar 704, even the endoscope 100 without an illumination means can be guided safely and easily into the abdominal cavity.

Figure 11A:
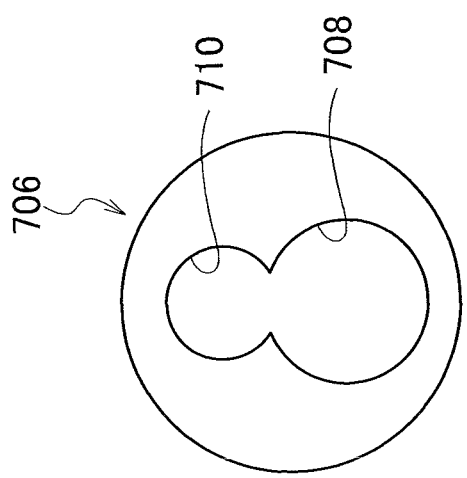
FIGS. 11A and 11B are plan views illustrating still another configuration example of the coupling fixtures.
Figure 11B:
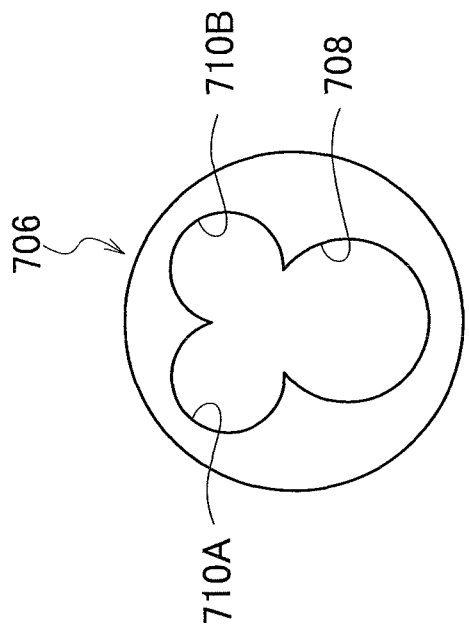

The configuration of the coupling fixtures 706 is not limited to the configuration illustrated in FIG. 9, and for example, configurations illustrated in FIGS. 10, 11A and 11B may also be employed.

FIG. 10 is a plan view illustrating another configuration example of the coupling fixtures 706. As illustrated in FIG. 10, the coupling fixture 706 has a plurality of second through holes 710A and 710B formed therein. According to this configuration, the insertion portions 202 of a plurality of the needle lights 200 can be integrated with the insertion portion 102 of the endoscope 100. As a consequence, it becomes possible to secure desired brightness when illumination light from only one needle light 200 cannot provide sufficient brightness. It is to be noted that the number of the second through holes 710 is not limited to two but may be three or more. Moreover, a plurality of the first through holes 708 may also be formed.

FIGS. 11A and 11B are plan views illustrating still another configuration example of the coupling fixtures 706. The configuration illustrated in FIG. 11A is in common with the configuration illustrated in FIG. 9 in that the first and second through holes 708 and 710 are formed but is different therefrom in that these through holes 708 and 710 are not separated nor independent from each other but are partially connected to each other. Similarly, the configuration illustrated in FIG. 11B is in common with the configuration illustrated in FIG. 10 in that the first through hole 708 and the second through holes 710A and 710B are formed, but is different therefrom in that these through holes 708, 710A, and 710B are not separated nor independent from each other but are partially connected to each other. With use of any one of these coupling fixtures 706, it is possible to integrate the insertion portion 102 of the endoscope 100 with the insertion portion 202 of the needle light 200.

In the present embodiment, the aforementioned coupling fixtures 706 are preferably used as a means to integrate the insertion portion 102 of the endoscope 100 with the insertion portion 202 of the needle light 200, but it is not limited thereto, integration may be achieved by, for example, collectively inserting the insertion portion 102 of the endoscope 100 and the insertion portion 202 of the needle light 200 into an oblong cylindrical insertion supporting tool (tube-like tool). Moreover, the insertion portion 102 of the endoscope 100 and the insertion portion 202 of the needle light 200 may integrally be bound with a string-like member with use of a treatment tool. However, an in the present embodiment, the configuration using the coupling fixtures 706 is the simplest and more preferable.

Referring again to FIG. 5, a description is continued. After the scope unit 700 is inserted into the abdominal cavity through the first opening 702, another needle light 200 is inserted into the abdominal cavity through a second opening 712 formed at a position different from the first opening 702 (for example, an upper right portion in the abdomen) as illustrated in FIG. 6B (Step S12 of FIG. 5).

At this point, the trocar 300 (needle light trocar) illustrated in FIG. 4 is inserted through the second opening 712, and the another needle light 200 is inserted into the abdominal cavity through the trocar 300. The same apply to a later-described third opening 714.

Consequently, the insertion portions 202 of two needle lights 200 are now inside the abdominal cavity. Accordingly, even when one of the needle lights 200 is pulled out, the other needle light 200 can illuminate inside the body cavity, which can prevent the endoscope 100 without an illumination means from being put in an unobservable state.

Next, as illustrated in FIG. 6C, the insertion portion 202 of the needle light 200 is pulled out from the first opening 702 (Step S14 of FIG. 5).

Next, as illustrated in FIG. 6C, through a third opening 714 formed at a position different from the first and second openings 702 and 712 (for example, a central left portion in the abdomen), the insertion portion 202 of the needle light 200 pulled out from the first opening 702 is inserted into the abdominal cavity (Step S16 of FIG. 5).

Next, the insertion portion 102 of the endoscope 100 is pulled out from the first opening 702 (Step S18 of FIG. 5).

Next, as illustrated in FIG. 6D, the insertion portion 102 of the endoscope 100 is inserted through a fourth opening 716 formed at a position different from the first to third openings 702, 712 and 714 (for example, a central right portion in the abdomen) (Step S20 of FIG. 5).

The fourth opening 716 is an opening formed for inserting the insertion portion 102 of the endoscope 100 into the abdominal cavity. A trocar 718 (for example, 3-mm trocar) of a size corresponding to the external diameter of the insertion portion 102 of the endoscope 100 is inserted through the fourth opening 716, and the insertion portion 102 of the endoscope 100 is inserted into the abdominal cavity through the trocar 718.

Next, as illustrated in FIG. 6D, a treatment tool 720 such as 5-mm forceps is inserted into the abdominal cavity through the first opening 702 (Step S22 of FIG. 5).

By placing the insertion portion 102 of the endoscope 100 and the insertion portion 202 of the needle light 200 into the abdominal cavity of the patient in this way, specified examination, treatment and the like can be performed.

According to the present embodiment as described above, even in the case where the endoscope 100 does not have an illumination means, when the insertion portion 102 of the endoscope 100 and the insertion portion 202 of the needle light 200 are inserted into a body cavity such as the abdominal cavity in accordance with the procedures illustrated in FIG. 5, it becomes possible to safely place the insertion portion 102 of the endoscope 100 and the insertion portion 202 of the needle light 200 at desired positions while constantly observing and illuminating the inside of the body cavity. Moreover, even when the number of openings formed on the body wall increases, the second to fourth openings 712, 714 and 716, which are openings for guiding the insertion portion 102 of the endoscope 100 and the insertion portion 202 of the needle light 200 into the body cavity, can be made smaller than the first opening 702. As a result, it becomes possible to make a postoperative scar less noticeable and to reduce the burden of the patient, so that low invasiveness can be achieved.

Moreover, since an opening can be formed at an arbitrary position corresponding to a treatment target region and access can be made thereto, operation is not constrained and therefore observation and treatment of the treatment target region can be facilitated. Moreover, it becomes possible to achieve easy access to a treatment target region where direct access from one opening is impossible, so that stable treatment can be performed.

Now, a method of inserting the trocar 300 in the present embodiment is explained with reference to FIGS. 12A to 12C. FIGS. 12A to 12C are explanatory views illustrating a method of inserting the trocar 300.

First, as illustrated in FIG. 12A, the inner needle 304 is incorporated into the coat pipe 302, and in this state, the front end of the trocar 300 is inserted from a body surface skin that is an exterior surface of an abdominal wall to a specified depth position inside the abdominal wall along a direction (first direction) generally vertical to the body surface skin. In this case, the front end of the trocar 300 is inserted until the front end of the trocar 300 (the front end portion 308 of the inner needle 304 projected from the front end of the coat pipe 302 to be specific) reaches a middle position of a muscle layer (between the body surface skin and a peritoneum and preferably between a mid-position of the muscle layer and the peritoneum).

Next, the trocar 300 whose front end was inserted to the middle of the muscle layer is inclined as illustrated in FIG. 12B. More specifically, the trocar 300 is pushed down aslant so that the body portion 316 of the coat pipe 302 is closer to the body surface skin, with a longitudinal shaft direction of the insertion portion (the rigid portion 312 and the flexible portion 314) of the coat pipe 302 being in an oblique direction with respect to the body surface skin.

Next, as illustrated in FIG. 12C, while the trocar 300 is in the state of being inclined, the front end of the trocar 300 is inserted in a direction (second direction) oblique with respect to the body surface skin. As a consequence, the front end of the inner needle 304 inserted into the coat pipe 302 passes the peritoneum and is inserted to a depth position where the front end of the coat pipe 302 is inside the abdominal cavity. Then, the inner needle 304 is removed from the coat pipe 302, so that a pathway for guiding the insertion portion 202 of the needle light 200 into the abdominal cavity through the insertion passage 322 inside the coat pipe 302 is secured. Then, the insertion portion 202 of the needle light 200 is inserted into the insertion passage 322 of the coat pipe 302, so that the front end of the insertion portion 202 of the needle light 200 can be guided into the abdominal cavity.

According to the insertion method illustrated in FIGS. 12A to 12C, when the trocar 300 is stuck into the abdominal cavity, the front end of the trocar 300 is inserted to the middle position (middle of the muscle layer) inside the abdominal wall along the direction (first direction) generally vertical to the body surface skin, and then the front end of the trocar 300 is inserted from the middle position inside the abdominal wall into the abdominal cavity beyond the peritoneum along the direction (second direction) forming a more acute angle with the body surface skin than the first direction. In this case, as for the first direction, an angle of inclination (insertion angle) α1 with respect to the body surface skin is preferably 70 degrees to 110 degrees, more preferably 80 degrees to 100 degrees, and particularly preferably 85 degrees to 95 degrees. As for the second direction, an angle of inclination (insertion angle) α2 with respect to the body surface skin is preferably 60 degrees or less, more preferably 45 degrees or less, and particularly preferably 30 degrees or less.

By inserting the trocar 300 into the abdominal cavity in this way, the rigid portion 312 of the coat pipe 302 (a portion formed in a region which is enclosed with the body wall) receives larger resistance from the muscle layer as illustrated with arrows in FIG. 12B and FIG. 12C. Accordingly, as compared with the case where the trocar 300 is inserted without changing the insertion direction, the trocar 300 stuck into the abdominal cavity is reliably fixed. As a result, without being influenced by body motions and external vibrations, the needle light 200 inserted into the trocar 300 is stabilized, which makes it possible to prevent a target organ or other organs around the target organ from being damaged. Moreover, the needle light 200 inserted into the trocar 300 can be fixed aslant, so that illumination to the treatment target region can stably be emitted. Further, if the needle light 200 can be fixed, operation thereof is unnecessary, and this makes it possible to perform techniques without the necessity of adding operation of the needle light 200 to general laparoscopic surgery, i.e., without the necessity of increasing an operator to operate the needle light 200.

It is to be noted that the insertion method illustrated in FIGS. 12A to 12C is applied not only to the trocar 300 but is similarly applicable to any medical instruments which can directly be stuck (punctured) from the body surface skin of a patient. For example, the method can be applied to a type of needle light which is directly stuck from the body surface skin without use of a trocar as seen in another embodiment described later, in which the same operation effects as in the case of sticking the trocar 300 can be obtained.

Second Embodiment

Figure 13:
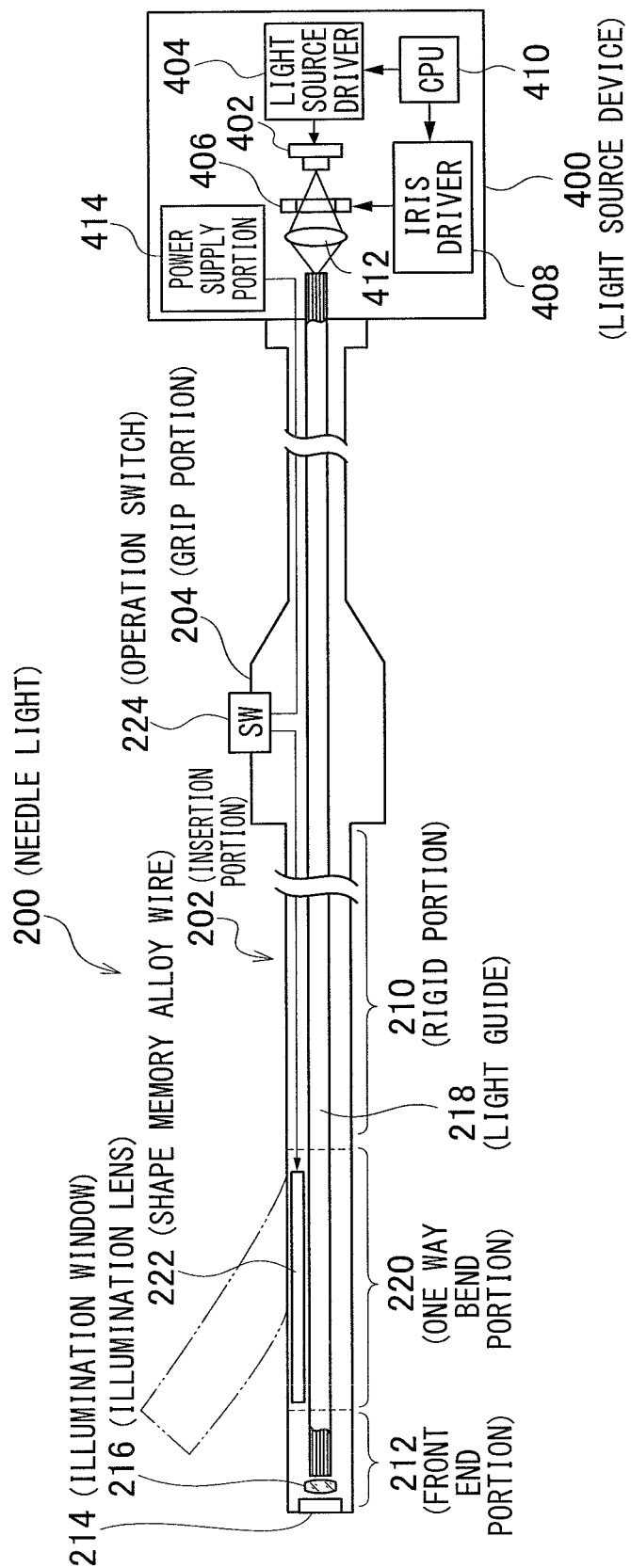
FIG. 13 is a schematic view illustrating a configuration example of a needle light according to a second embodiment.

FIG. 13 is a schematic view illustrating a configuration example of a needle light according to a second embodiment. In FIG. 13, component members in common with those in FIG. 3 are designated by identical reference numerals to omit a description thereof.

As illustrated in FIG. 13, the insertion portion 202 of the needle light 200 according to the second embodiment has a bend portion (one way bend portion) 220 bendable in one direction provided between the rigid portion 210 and the front end portion 212. A shape memory alloy wire 222 in a linear shape is inserted into the one way bend portion 220. The shape memory alloy wire 222 has a two-way shape memory effect that is to contract its length by heating and to expand its length by cooling so as to restore its original length. The grip portion 204 has an operation switch 224 provided for ON/OFF control of current application to the shape memory alloy wire 222. The shape memory alloy wire 222 is electrically connected to a power supply portion 414 provided inside the light source device 400 through the operation switch 224. Accordingly, when current is applied to the shape memory alloy wire 222 in response to operation of the operation switch 224, the shape memory alloy wire 222 is heated and put in a memorized shape that is a shape contracted in the shaft direction, so that the one way bend portion 220 is bent in a desired direction. When current application to the shape memory alloy wire 222 is stopped, the shape memory alloy wire 222 is cooled and restored to the original state, so that the one way bend portion 220 is in the state of extending straight.

According to the configuration having such a one way bend portion 220 provided in the insertion portion 202, an illuminating direction can easily be adjusted to a desired direction. It is to be noted that the bend portion may be bendable not in one direction but in a plurality of directions (for example, two ways and four ways). However, unlike the endoscope 100, the needle light 200 does not have vertical and horizontal orientation; if the insertion portion 202 is rotated around its shaft and moved backward and forward in the shaft direction by operation of an operator, the illuminating direction can be adjusted to a desired direction only with one way bend; and in the case where a multi-way bend portion is provided, the diameter in the insertion portion 202 of the needle light 200 tends to increase and therefore, the configuration having the one way bend portion 220 as that in the present embodiment is preferable. In this configuration, the diameter of the insertion portion 202 of the needle light 200 can be decreased as compared with the configuration having the multi-way bend portion, so that the burden of a patient can be reduced. Moreover, since the front end portion 212 coupled to the front end of the one way bend portion 220 has flexibility, it becomes possible to prevent organ damage caused by the front end portion 212 coming into contact an organ when the one way bend portion 220 is bent.

In the present embodiment, the insertion portion 202 of the needle light 200 is configured to be bent by heating or cooling of the shape memory alloy wire 222, but it is not limited thereto, the insertion portion 202 of the needle light 200 may be configured to be bent by press and pull operation of a general wire which is inserted and placed inside the insertion portion 202 of the needle light 200. Since the configuration to bend the insertion portion 202 with use of a general wire is publicly known, a description thereof is omitted.

Third Embodiment

Figure 14:
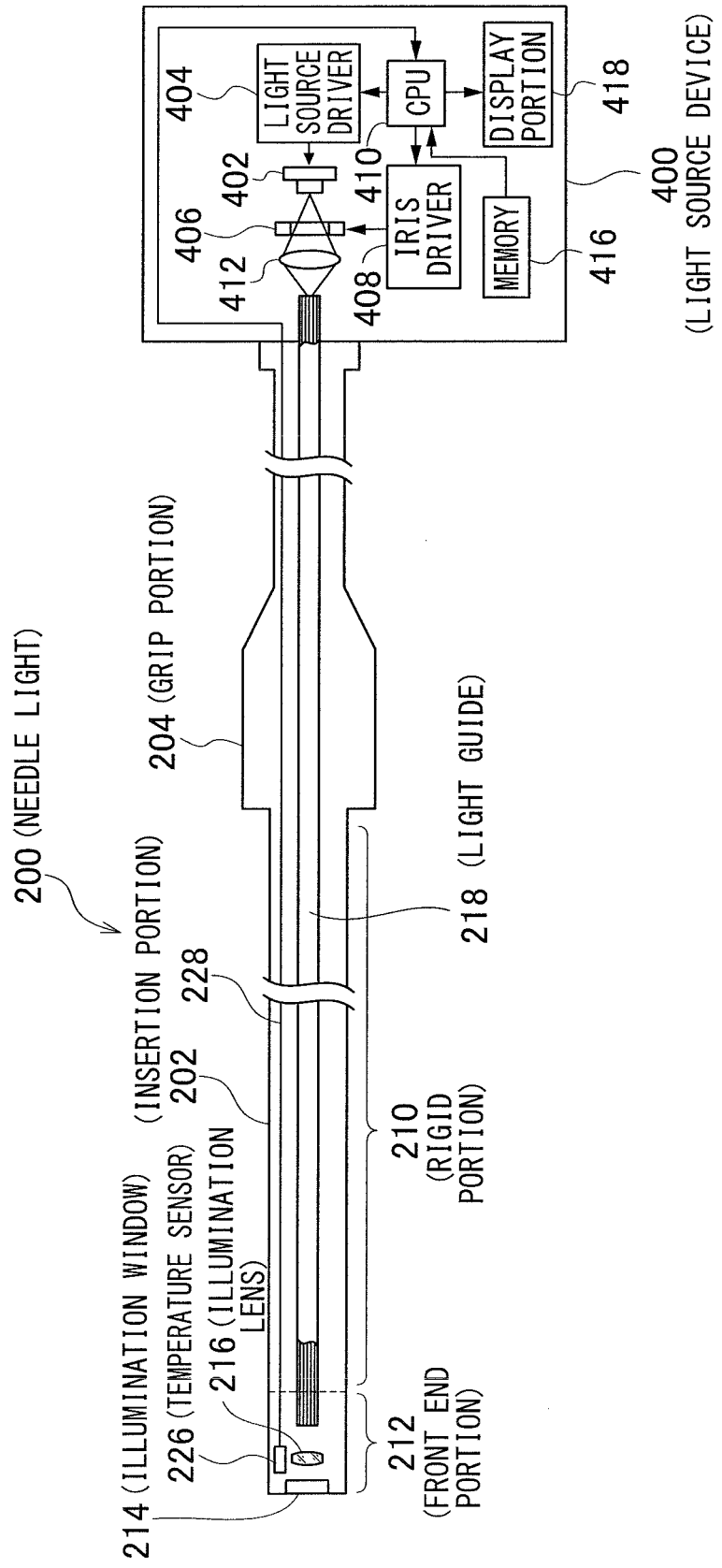
FIG. 14 is a schematic view illustrating a configuration example of a needle light according to a third embodiment.

FIG. 14 is a schematic view illustrating a configuration example of a needle light according to a third embodiment. In FIG. 14, component members in common with those in FIG. 3 are designated by identical reference numerals to omit a description thereof.

As illustrated in FIG. 14, the needle light 200 according to the third embodiment has a temperature sensor 226 built in the front end portion 212 of the insertion portion 202. The temperature sensor 226 detects temperature of the front end portion 212, and outputs the detected temperature to the CPU 410 of the light source device 400 through the signal line 228.

The CPU 410 of the light source device 400 obtains temperature change (temperature change rate) per unit time based on the temperature detected by the temperature sensor 226, and compares the temperature change rate with a reference value stored in a memory 416. When the temperature change rate exceeds the reference value as a result of comparison, the CPU 410 determines that the front end portion 212 of the insertion portion 202 may be in contact with an organ, so that light volume control is performed on the light source driver 404 or the iris driver 408 to reduce the light volume of illumination light or to turn off the light source. The CPU 410 also displays an alarm on a display portion 418. A warning lamp may also be lit or flashed, and an alarm sound may be issued.

As described above, according to the present embodiment, the light volume of illumination light is controlled based on the result of measurement with the temperature sensor 226 which is built in the front end portion 212 of the insertion portion 202. Accordingly, when the front end portion 212 of the insertion portion 202 is in contact with an organ and is in an abnormally heated condition thereby, it becomes possible to reduce the light volume of illumination light or to turn off the light source. This makes it possible to prevent organ damage caused by heat burn and the like from occurring. Moreover, an operator can easily grasp whether or not the front end portion 212 of the insertion portion 202 is in contact with an organ, so that the operator can determine whether or not the position of the front end portion 212 of the insertion portion 202 needs to be adjusted.

In the present embodiment, as the temperature sensor 226, a thermistor, a thermocouple, a resistance bulb and the like may be used. Of these, the thermocouple is preferably used to constitute the temperature sensor 226. The thermocouple uses a phenomenon (Seebeck effect) of thermoelectromotive force being generated due to a temperature difference between two dissimilar metal junctions.

Figure 15:
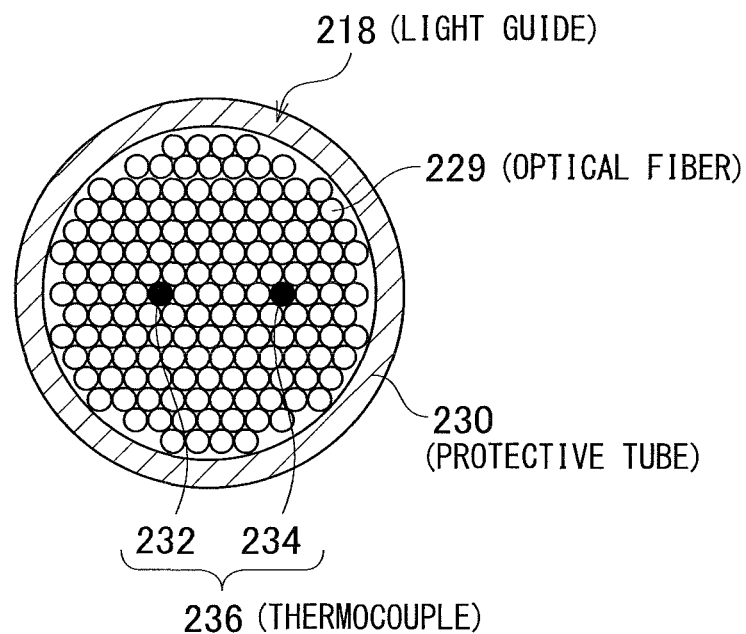
FIG. 15 is a cross sectional view illustrating a configuration example of a light guide having a thermocouple provided therein.

FIG. 15 is a cross sectional view illustrating a configuration example of a light guide 218 having a thermocouple provided therein. As illustrated in FIG. 15, the light guide 218 has a cross sectional shape formed by binding a plurality of optical fibers 229 into a circular shape and coating an outer peripheral portion thereof with a protective tube 230 formed of an elastic material such as silicone. Two metal wires 232 and 234 made of different materials are buried in a plurality of the optical fibers 229, and these metal wires 232 and 234 constitute a thermocouple 236. The thermocouple 236 has a temperature measuring junction (not illustrated) connected to these two metal wires 232 and 234. The temperature measuring junction is provided at an arbitrary position on the front end portion 212 of the insertion portion 202.

Figure 16:
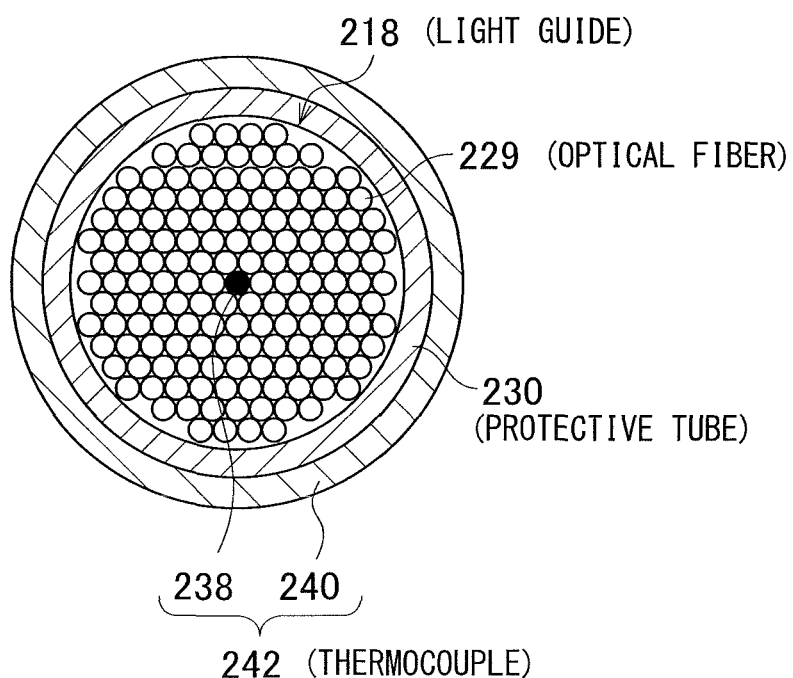
FIG. 16 is a cross sectional view illustrating another configuration example of the light guide having a thermocouple provided therein.

FIG. 16 is a cross sectional view illustrating another configuration example of the light guide 218 having a thermocouple provided therein. In the configuration illustrated in FIG. 16, one metal wire 238 is buried in a plurality of the optical fibers 229 that constitute the light guide 218, while an outer cylinder pipe 240 made of metal is provided on an outer peripheral portion of the protective tube 230 coating the light guide 218. The thermocouple 242 includes the metal wire 238 and the outer cylinder pipe 240. The thermocouple 242 has a temperature measuring junction (not illustrated) where the metal wire 238 and the outer cylinder pipe 240 are connected at an arbitrary position on the front end portion 212 of the insertion portion 202.

Thus, according to the configuration using the thermocouple as the temperature sensor 226, it becomes possible to place the thermocouple with use of the light guide 218 as illustrated in FIG. 15 or FIG. 16. Consequently, it becomes possible to place the temperature sensor 226 in the front end portion 212 of the insertion portion 202 without increasing the external diameter of the front end portion 212 of the insertion portion 202. This makes it possible to easily determine whether or not the front end portion 212 of the insertion portion 202 is in contact with an organ while reduction (downsizing) in the diameter of the front end portion 212 of the insertion portion 202 is achieved, so that organ damage caused by heat burn and the like can be prevented.

Fourth Embodiment

The fourth embodiment includes a means to integrate, inside a body cavity, the front end portion of the insertion portion 102 in the endoscope 100 and the front end portion of the insertion portion 202 in the needle light 200, which are inserted into the body cavity from different openings.

Figure 17A:
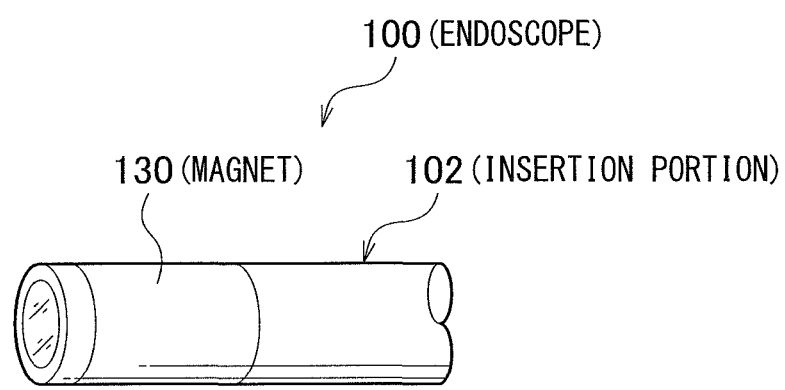
FIGS. 17A and 17B are schematic views illustrating a configuration of a front end portion of an insertion portion in an endoscope according to a fourth embodiment.
Figure 17B:
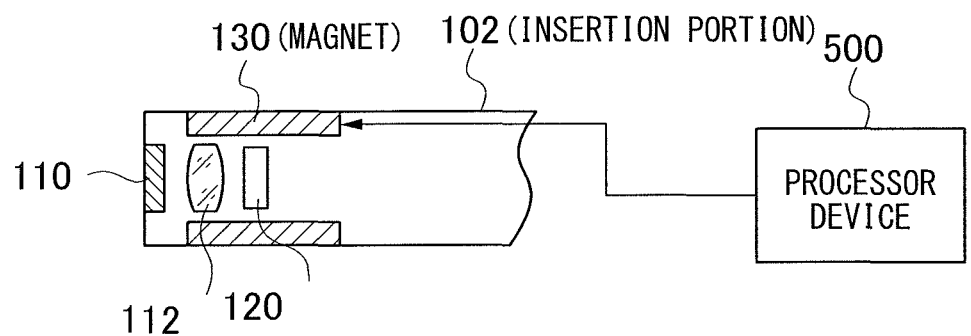

FIGS. 17A and 17B are schematic views illustrating a configuration of the front end portion of the insertion portion in the endoscope according to the fourth embodiment. In FIGS. 17A and 17B, component members in common with those in FIG. 3 are designated by identical reference numerals to omit a description thereof.

As illustrated in FIGS. 17A and 17B, a cylindrical magnet 130 is provided on an outer peripheral surface of the front end portion of the insertion portion 102 in the endoscope 100. The magnet 130 is made of an electromagnet. The magnet 130 is connected to the processor device 500 through a power cable (not illustrated), and a power application state and a non-power application state of the magnet 130 are switched in response to presence/absence of electric power supply from the processor device 500. Accordingly, the magnet 130 generates magnetism in the power application state, and does not generate magnetism in the non-power application state. The material of the magnet 130 is not limited to an electromagnet but may be a permanent magnet.

Figure 18A:
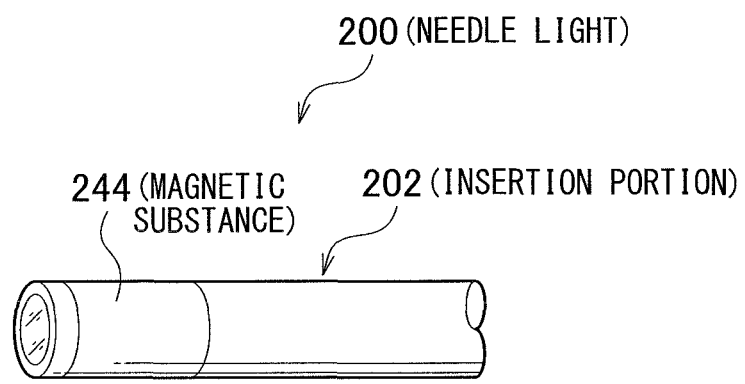
FIGS. 18A and 18B are schematic views illustrating a configuration of a front end portion of an insertion portion in a needle light according to the fourth embodiment.
Figure 18B:
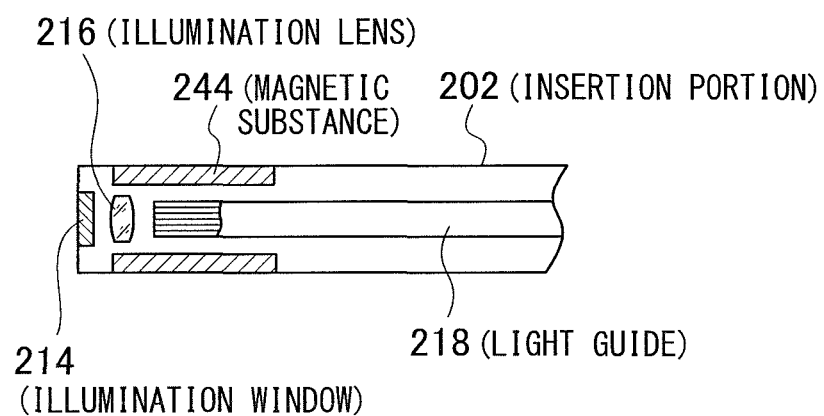

FIGS. 18A and 18B are configuration views illustrating a configuration of a front end portion of an insertion portion of a needle light according to the fourth embodiment. As illustrated in FIGS. 18A and 18B, a cylindrical magnetic substance 244 is provided on an outer peripheral surface of the front end portion of the insertion portion 202 of the needle light 200. The magnetic substance 244 is made of, for example, a magnetic member such as iron. Therefore, the magnetic substance 244 is attracted by magnetism generated by the magnet 130. The insertion portion 202 in the present embodiment is preferably configured with a flexible portion having flexibility.

Figure 19:
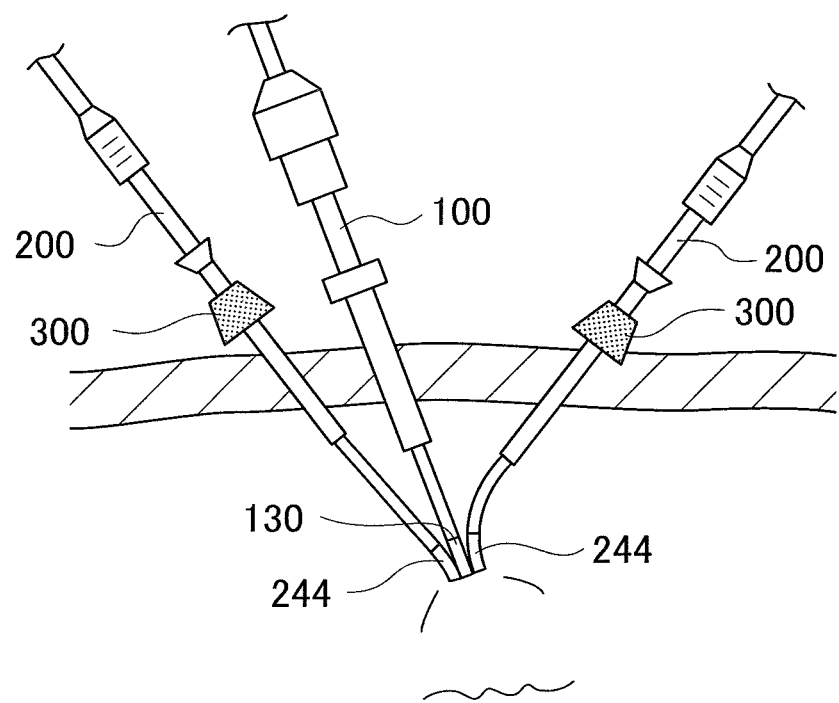
FIG. 19 is an explanatory view illustrating the front end portion of the insertion portion in the endoscope being integrated with the front end portion of the insertion portion in the needle light inside a body cavity.

A description is given of the functions of the present embodiment with reference to FIG. 19. FIG. 19 is an explanatory view illustrating the front end portion of the insertion portion in the endoscope being integrated with the front end portion of the insertion portion in the needle light inside a body cavity.

First, for example, through different openings formed in an abdomen, the insertion portion 102 of the endoscope 100 and the insertion portion 202 of the needle light 200 are inserted. Then, when an operation switch (not illustrated) provided on the grip portion 104 is turned ON, electric power is supplied to the magnet 130 from the processor device 500. As a consequence, the magnet 130 is put in the power application state and generates magnetism, so that the magnetic substance 244 is attracted to the magnet 130. As a result, as illustrated in FIG. 19, the insertion portion 102 in the endoscope 100 and the insertion portion 202 in the needle light 200 are integrated with each other by connecting the front end portions thereof.

For pulling out the insertion portion 102 of the endoscope 100 or the insertion portion 202 of the needle light 200 out of the abdominal cavity, when the operation switch is turned OFF, and the electric power supplied to the magnet 130 from the processor device 500 is stopped. This puts the magnet 130 in the non-power application state and stops generating magnetism, so that integration of the front end of the insertion portion 102 in the endoscope 100 and the front end of the insertion portion 202 in the needle light 200 is cancelled. This makes it possible to easily pull the insertion portion 102 of the endoscope 100 and the insertion portion 202 of the needle light 200 out of the body cavity.

As mentioned above, according to the present embodiment, the magnet 130 is provided on the insertion portion 102 of the endoscope 100, while the magnetic substance 244 is provided on the insertion portion 202 of the needle light 200, so that the front end portion of the insertion portion 102 in the endoscope 100 and the front end portion of the insertion portion 202 in the needle light 200 can be integrated inside the body cavity. Consequently, when one of the insertion portion 102 of the endoscope 100 and the insertion portion 202 of the needle light 200 is moved, the other is also moved integrally; and therefore it is not necessary to operate these portions separately, which makes it possible to eliminate complicated operation as well as to prevent damage of an organ. This makes it possible to secure operability and safety of the endoscope and the illuminator inserted into a body cavity such as an abdominal cavity.

FIGS. 17A to 18B illustrate the configuration in which the magnet 130 is provided on the insertion portion 102 of the endoscope 100 while the magnetic substance 244 is provided on the insertion portion 202 of the needle light 200, but it is possible to apply an opposite configuration of the foregoing configuration, that is, the configuration in which a magnetic substance is provided on the insertion portion 102 of the endoscope 100 while a magnet is provided on the insertion portion 202 of the needle light 200, and still the same operational effects can be obtained.

Although a magnet is used in the present embodiment as a means to integrate the front end of the insertion portion 102 in the endoscope 100 with the front end of the insertion portion 202 in the needle light 200 inside a body cavity, it is not limited to this configuration, and the front ends of the respective insertion portions may be integrated with use of, for example, a string-like member (mechanical fixing means) such as a surgical thread.

Fifth Embodiment

Figure 20:
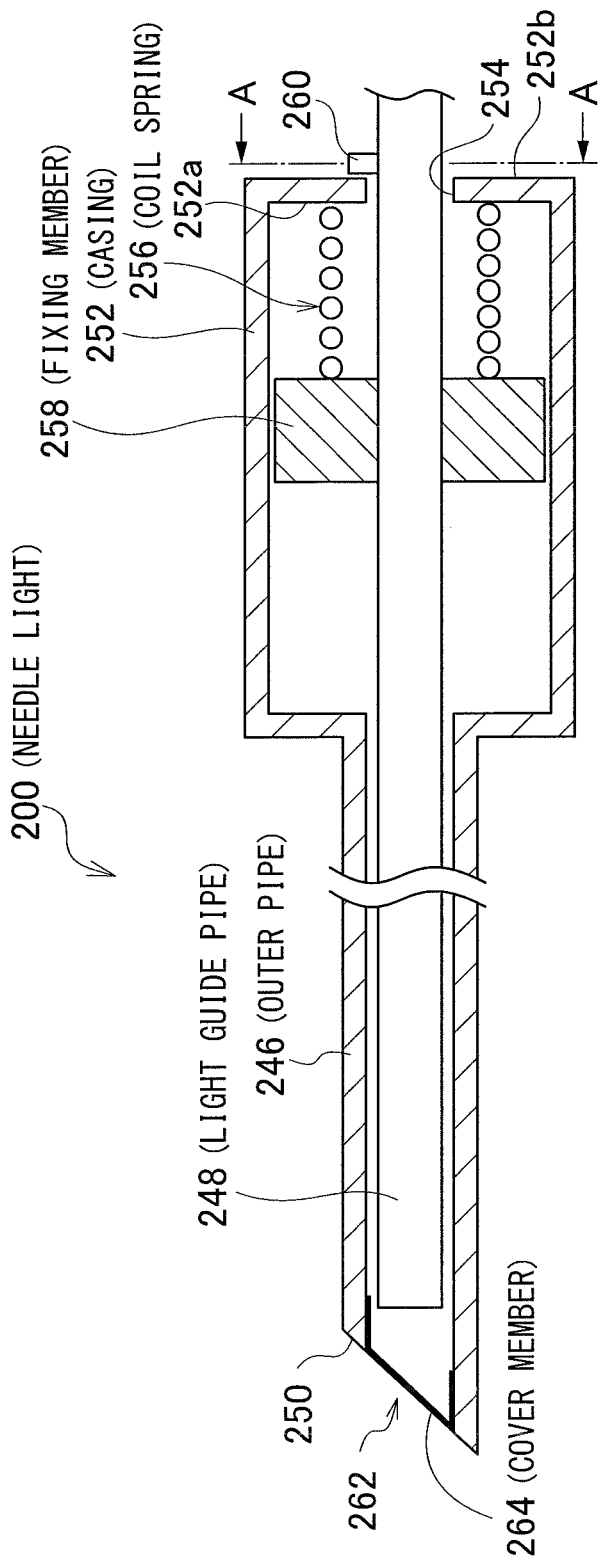
FIG. 20 is a schematic view illustrating a configuration example of a needle light according to a fifth embodiment.

FIG. 20 is a schematic view illustrating a configuration example of a needle light according to a fifth embodiment. In FIG. 20, component members in common with those in FIG. 3 are designated by identical reference numerals to omit a description thereof.

As illustrated in FIG. 20, a needle light 200 according to the fifth embodiment, which is of a type directly stuck into a body cavity from the body surface skin, includes an outer pipe 246 with a sharp front end and a light guide pipe 248 inserted into the outer pipe 246 so as to freely move back and forth.

The outer pipe 246 is constituted from, for example, a hard cylindrical body made of metal such as stainless steel and titanium, and a front end portion thereof is formed to be opened and has an edge portion 250 provided to have a sharp blade surface cut aslant with respect to the shaft direction.

The light guide pipe 248 is an illuminating member capable of emitting illumination light for illuminating the inside of a body cavity from the front end portion. A light guide and an illumination optical system (each of which is not illustrated) are provided inside the light guide pipe 248.

A casing 252 formed to have a hollow inside is coupled to the base end side of the outer pipe 246. The casing 252 is made of a cylindrical tube member formed to be thicker than the outer pipe 246, and the light guide pipe 248 is inserted into the casing 252 so as to freely move back and forth. A through hole 254 for inserting the light guide pipe 248 is formed on a wall surface of the base end side of the casing 252. The through hole 254 is configured to have an inner diameter slightly larger than an external diameter of the light guide pipe 248 so that the light guide pipe 248 freely moves back and forth.

Inside the casing 252, a coil spring 256 is provided as a biasing means configured to bias the light guide pipe 248 in a front end direction with respect to the outer pipe 246. The coil spring 256 is wound around an outer periphery of the light guide pipe 248. A base end of the coil spring 256 is in contact with an inner wall surface 252a of the base end side of the casing 252. A front end of the coil spring 256 is in contact with an end face of the base end side of a cylindrical fixing member 258 fixed to the light guide pipe 248. Consequently, the light guide pipe 248 is biased in the front end direction with respect to the outer pipe 246 with the biasing force of the coil spring 256.

A locking member 260, which can come into contact with an external wall surface 252b of the base end side of the casing 252, is provided on an outer peripheral portion of the base end side of the light guide pipe 248. The locking member 260, as illustrated in FIG. 20, comes into contact with the external wall surface 252b of the base end side of the casing 252 to lock the movement of the light guide pipe 248 in the front end direction in the state where the front end of the light guide pipe 248 is housed in the outer pipe 246 against biasing force of the coil spring 256.

Figure 21:
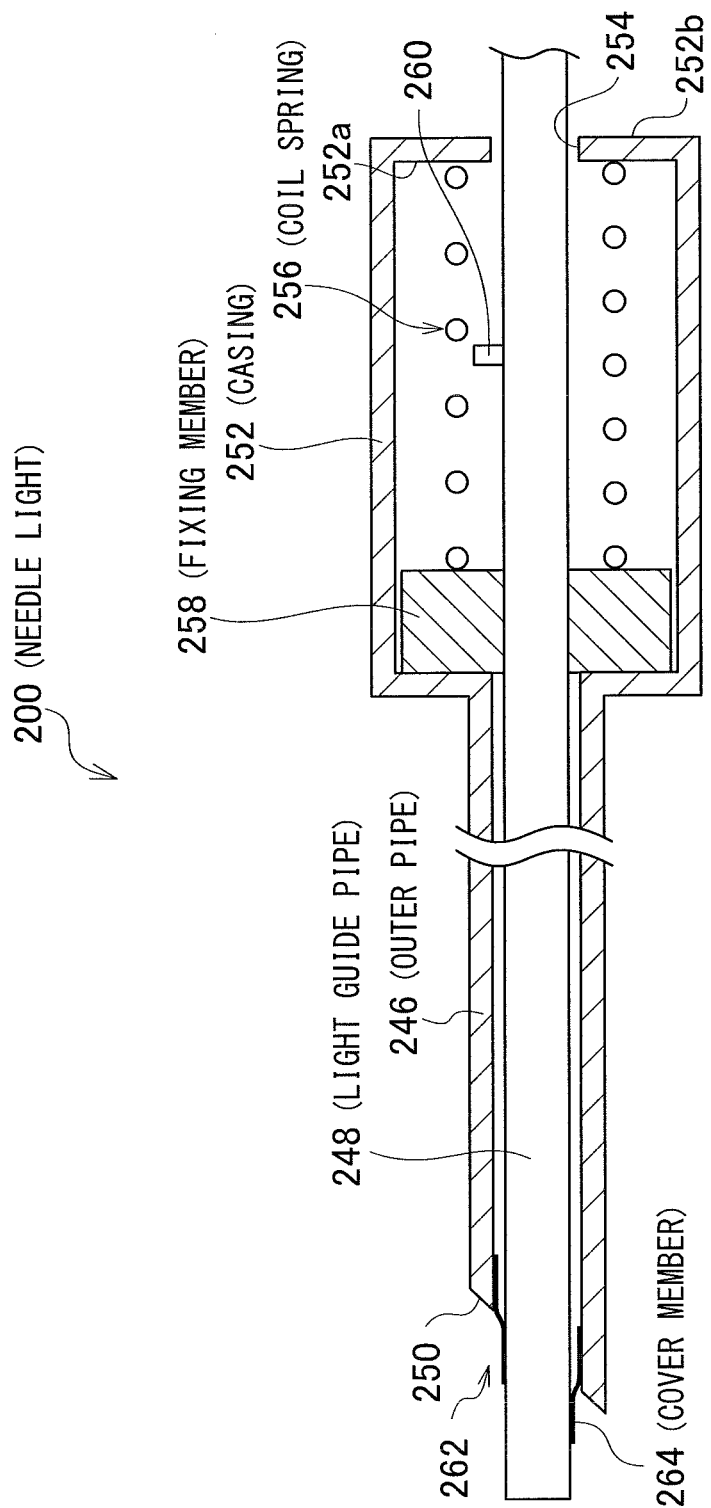
FIG. 21 is a schematic view illustrating a configuration example of the needle light according to the fifth embodiment.
Figure 22:
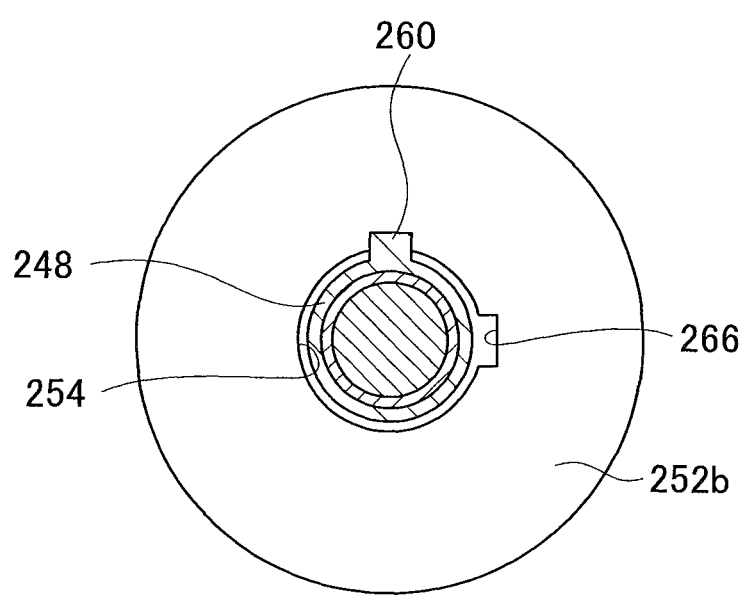
FIG. 22 is a cross sectional view along a line A-A in FIG. 20.

As illustrated in FIG. 22, the through hole 254 of the casing 252 is provided with an inserting groove 266 formed along a shaft direction at a phase position different from the locking member 260 of the light guide pipe 248. The inserting groove 266 is dimensioned so that the locking member 260 can be inserted therein. Accordingly, if the light guide pipe 248 is rotated relatively with respect to the casing 252 so as to coincide the phases of the locking member 260 and the inserting groove 266, the locking member 260 can pass through the inserting groove 266, by which the locked movement is unlocked. As a result, the light guide pipe 248 is made to be movable in the front end direction with the biasing force of the coil spring 256, so that the front end of the light guide pipe 248 is put in the state of projecting toward the front end side from a front end opening 262 of the outer pipe 246 as illustrated in FIG. 21.

The front end opening 262 of the outer pipe 246 is provided with a film-like (filmy) cover member (protective cover) 264 as a protective member for protecting the front end of the light guide pipe 248 housed in the front end opening 262. The cover member 264 is configured to have a breaking portion breakable when the front end of the light guide pipe 248 projects toward the front end side from the front end opening 262 of the outer pipe 246; and the material and thickness of the cover member 264 are properly selected depending on the biasing force of the coil spring 256.

A description is now given of the functions of the present embodiment with reference to FIGS. 23A to 23C. FIGS. 23A to 23C are explanatory views illustrating the needle light 200 of the present embodiment being directly stuck into an abdominal wall from the body surface skin.

First, as illustrated in FIG. 23A, in the state where the front end of the light guide pipe 248 is housed in the outer pipe 246 and the movement of the light guide pipe 248 in the front end direction is locked by the locking member 260, an edge portion 250 at the front end of the outer pipe 246 is brought into contact with the body surface skin. In this case, the front end opening 262 of the outer pipe 246 is closed by the cover member 264.

Next, as illustrated in FIG. 23B, the movement of the light guide pipe 248 in the front end direction locked by the locking member 260 is unlocked, and the front end of the outer pipe 246 is stuck toward the abdominal wall from the body surface skin. At this time, although the light guide pipe 248 is in the state of being biased in the front end direction with the biasing force of the coil spring 256, the front end of the light guide pipe 248 receives pressing force from an abdominal wall toward the base end side through the cover member 264. Accordingly, the front end of the light guide pipe 248 is put in the state of being pushed into the outer pipe 246. In this case, since the front end opening 262 of the outer pipe 246 is closed by the cover member 264, adhering substances (fat, muscle, blood and the like) are prevented from adhering to the front end of the light guide pipe 248.

When the front end of the outer pipe 246 penetrates the abdominal wall and reaches the inside of the abdominal cavity as illustrated in FIG. 23C, pressing force received from the abdominal wall is lost. Therefore, the front end of the light guide pipe 248 breaks through the cover member 264 due to the biasing force of the coil spring 256 and is put in the state of projecting toward the front end side from the front end opening 262 of the outer pipe 246.

According to the present embodiment as described, when the front end of the outer pipe 246 penetrates the body wall and reaches a body cavity at the time of piercing the needle light 200 into the body cavity such as the abdominal cavity, the front end portion of the light guide pipe 248 breaks the cover member 264 with the biasing force of the coil spring 256, and automatically projects toward the front end direction from the front end opening 262 of the outer pipe 246. At this time, since the front end opening 262 of the outer pipe 246 is closed by the cover member 264 while the front end of the outer pipe 246 is penetrating the body wall, adhering substances (fat, muscle, blood and the like) are prevented from adhering to the front end of the light guide pipe 248 housed in the outer pipe 246. Therefore, it becomes possible to solve failures caused by the adhering substances adhering to the front end of the light guide pipe 248 and to pierce the needle light 200 into the body cavity by easy operation.

In the present embodiment, the cover member 264 is preferably made of an elastic membrane. When the front end of the outer pipe 246 is inside the body wall, it becomes possible to prevent the cover member 264 from breaking before the front end of the outer pipe 246 penetrates the body wall and reaches into the body cavity even if some pressure change occurs in a pressure difference between pressing force of a base end direction that the cover member 264 receives from a body wall and pressing force of a front end direction received from the front end of the light guide pipe 248. Therefore, it becomes possible to reliably prevent the adhering substances from adhering to the front end of the light guide pipe 248.

Although the present embodiment illustrates the configuration using the cover member 264 breakable with the biasing force of the coil spring 256, it is not limited thereto, and a configuration using a cover member having an opening/closing portion that is openable and closable such as a door and a valve may also be employed for example. In such a configuration as in the present embodiment, when the front end of the outer pipe 246 penetrates a body wall and reaches into a body cavity, the front end portion of the light guide pipe 248 automatically projects toward the front end direction from the front end opening 262 of the outer pipe 246 by putting the cover member 264 in an opened state with the biasing force of the coil spring 256.

Figure 24:
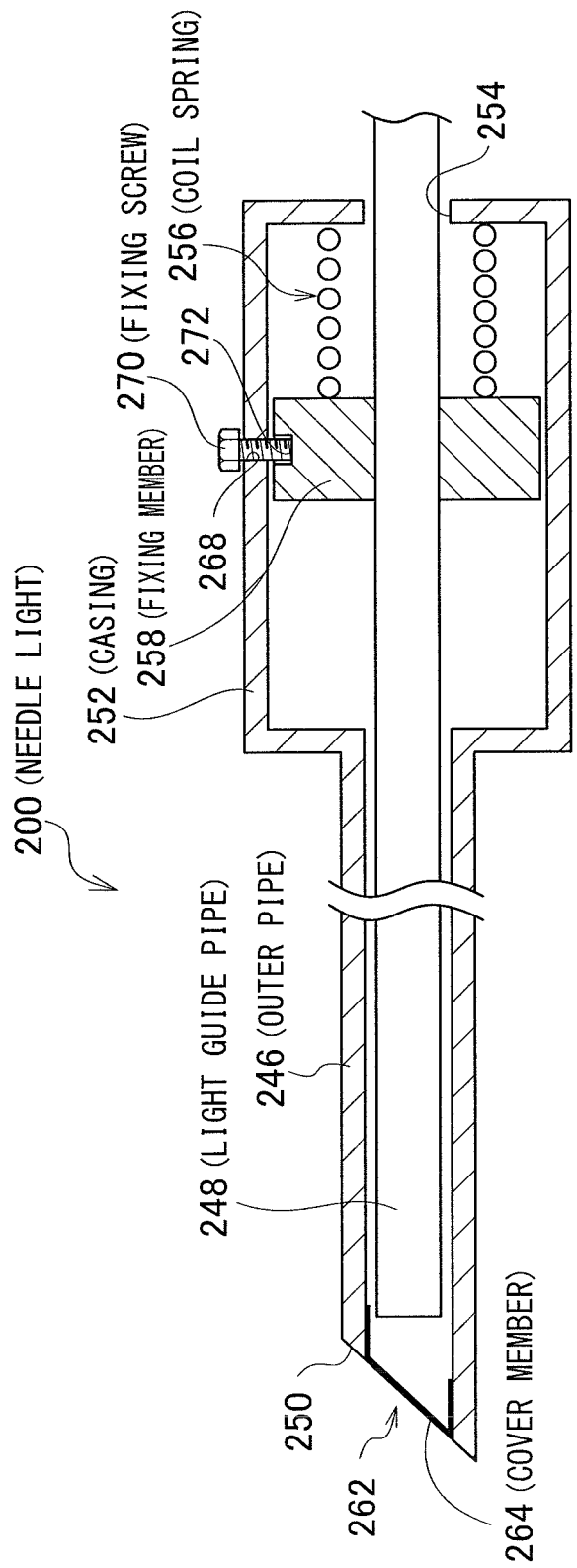
FIG. 24 is a schematic view illustrating another configuration example of the needle light according to the fifth embodiment.

Although, in the present embodiment, the locking member 260 provided on the outer peripheral portion of the base end side of the light guide pipe 248 is configured to come into contact with the external wall surface 252b of the base end side of the casing 252 as a means for locking the movement of the light guide pipe 248 in the front end direction against the biasing force of the coil spring 256, it is not limited thereto, and a configuration illustrated in FIG. 24 may be employed for example.

FIG. 24 is a schematic view illustrating another configuration example of the needle light according to the fifth embodiment. In FIG. 24, component members in common with those in FIG. 20 are designated by identical reference numerals to omit a description thereof.

In the configuration illustrated in FIG. 24, a screw hole (female screw) 268 is formed by penetrating the outer peripheral surface of the casing 252. A fixing screw (male screw) 270 is screwed into the screw hole 268. When the fixing screw 270 is fastened, the front end of the fixing screw 270 is put in the state of projecting to an inner peripheral surface of the casing 252 and engaging with an engagement groove 272 formed on the outer peripheral surface of the fixing member 258. As a consequence, as in the case of FIG. 20, the movement of the light guide pipe 248 in the front end direction is locked in the state where the front end of the light guide pipe 248 is housed in the outer pipe 246 against the biasing force of the coil spring 256.

When the fixing screw 270 is loosened, the engagement between the front end of the fixing screw 270 and the engagement groove 272 is cancelled. As a result, the light guide pipe 248 is made to be movable in the front end direction with the biasing force of the coil spring 256, so that the front end of the light guide pipe 248 is put in the state of projecting toward the front end side from the front end opening 262 of the outer pipe 246 as in the case of FIG. 21.

According to the configuration illustrated in FIG. 24, operating the fixing screw 270 makes it possible to easily unlock the movement of the light guide pipe 248 locked in the front end direction.

In the foregoing, although the method of placing the medical insertion instruments into a body cavity according to the present invention has been described in detail, it should be understood that the present invention is not limited to the examples disclosed, and various modifications and arrangements which come within the meaning of the present invention are possible.

In each of the above embodiments, although a description has been given of the case where the endoscope is applied to electronic endoscopes (electronic scopes) as one example, the endoscope of the present invention is also applicable to optical endoscopes (fiber scopes).

Further, in each of the above embodiments, although a description has been given of the case of applying the present invention to the endoscope without an illumination means, the endoscope of the present invention is applicable to, for example, an endoscope including an auxiliary illuminating means capable of emitting auxiliary illumination light. In the case of the endoscope including an auxiliary illuminating means, reduction in diameter can be achieved as compared with the conventional general endoscopes, and the effects of the present invention can sufficiently be demonstrated.

What is claimed is:

1. A method of placing medical insertion instruments in a body cavity, comprising:
    a first step of inserting, into the body cavity through a first opening formed on a body wall in an abdomen, an endoscope together with a first illuminator, wherein the endoscope is configured to observe an inside of the body cavity, the endoscope and the first illuminator being removably coupled during ordinary use, wherein the endoscope itself does not comprise an illumination instrument, and wherein the first illuminator is configured separately from the endoscope to emit illumination light to illuminate the inside of the body cavity;
    a second step of inserting, into the body cavity through a second opening formed on the body wall in the abdomen at a position different from the first opening, a second illuminator configured separately from the endoscope to emit illumination light to illuminate the inside of the body cavity, after the first step has been performed; and
    a third step of pulling out the first illuminator from the first opening and inserting the first illuminator into the body cavity through a third opening formed on the body wall at a position different from the first and second openings, after the second step has been performed.

2. The method according to claim 1, further comprising a fourth step of pulling out the endoscope from the first opening and inserting the endoscope into the body cavity through a fourth opening formed on the body wall at a position different from the first to third openings, after the third step has been performed.

3. The method according to claim 2, further comprising a fifth step of inserting a treatment tool into the body cavity through the first opening after the endoscope is pulled out, after the fourth step has been performed.

4. The method according to claim 3, wherein the fifth step is performed while observing and illuminating the body cavity with the endoscope, and at least one of the first illuminator and the second illuminator.

5. The method according to claim 2, wherein the fourth opening is smaller than the first opening.

6. The method according to claim 2, wherein the second to fourth openings are smaller than the first opening.

7. The method according to claim 2, wherein the fourth step is performed while observing and illuminating the body cavity with the endoscope, and at least one of the first illuminator and the second illuminator.

8. The method according to claim 1, wherein the second opening is smaller than the first opening.

9. The method according to claim 1, wherein the third opening is smaller than the first opening.

10. The method according to claim 1, wherein an insertion portion of the endoscope that is inserted into the body cavity has an external diameter of 3 mm or less.

11. The method according to claim 1, wherein insertion portions of the first and second illuminators that are inserted into the body cavity have an external diameter of 3 mm or less.

12. The method according to claim 1, wherein in the first step, the endoscope and the first illuminator are inserted into the body cavity via a trocar.

13. The method according to claim 1, wherein the second step is performed while observing and illuminating the body cavity with the endoscope, and at least one of the first illuminator and the second illuminator.

14. The method according to claim 1, wherein the third step is performed while observing and illuminating the body cavity with the endoscope, and at least one of the first illuminator and the second illuminator.

* * * * *

UNITED STATES PATENT AND TRADEMARK OFFICE
CERTIFICATE OF CORRECTION

PATENT NO. : 9,839,349 B2
APPLICATION NO. : 14/046461
DATED : December 12, 2017
INVENTOR(S) : Takumi Dejima et al.

Page 1 of 1

It is certified that error appears in the above-identified patent and that said Letters Patent is hereby corrected as shown below:

On the Title Page

At item (71), Applicants, change "FUJIFILM Corporation, Tokyo (JP); THE INSTITUTE FOR CANCER RESEARCH, Philadelphia, PA (US)" to --FUJIFILM Corporation, Tokyo (JP); THE INSTITUTE FOR CANCER RESEARCH d/b/a FOX CHASE CANCER CENTER, Philadelphia, PA (US)--.

At item (73), Assignees, change "FUJIFILM Corporation, Tokyo (JP); THE INSTITUTE FOR CANCER RESEARCH, Philadelphia, PA (US)" to --FUJIFILM Corporation, Tokyo (JP); THE INSTITUTE FOR CANCER RESEARCH d/b/a FOX CHASE CANCER CENTER, Philadelphia, PA (US)--.

Signed and Sealed this
Twenty-fourth Day of April, 2018

Andrei Iancu
*Director of the United States Patent and Trademark Office*